US008477316B2

(12) United States Patent
Holzapfel

(10) Patent No.: US 8,477,316 B2
(45) Date of Patent: Jul. 2, 2013

(54) INTERFEROMETER SYSTEM AND METHOD FOR ITS OPERATION

(75) Inventor: Wolfgang Holzapfel, Obing (DE)

(73) Assignee: Dr. Johannes Heidenhain GmbH, Traunreut (DE)

( * ) Notice: Subject to any disclaimer, the term of this patent is extended or adjusted under 35 U.S.C. 154(b) by 682 days.

(21) Appl. No.: 12/743,964

(22) PCT Filed: Oct. 1, 2008

(86) PCT No.: PCT/EP2008/008341
§ 371 (c)(1),
(2), (4) Date: May 20, 2010

(87) PCT Pub. No.: WO2009/065463
PCT Pub. Date: May 28, 2009

(65) Prior Publication Data
US 2010/0268499 A1    Oct. 21, 2010

(30) Foreign Application Priority Data
Nov. 21, 2007  (DE) .......................... 10 2007 055 665

(51) Int. Cl.
*G01B 11/02*  (2006.01)
(52) U.S. Cl.
USPC .......................................... 356/498; 356/517
(58) Field of Classification Search
USPC ......................... 356/496, 498, 500, 517, 73
See application file for complete search history.

(56) References Cited

U.S. PATENT DOCUMENTS

| 3,734,623 | A | 5/1973 | Wolber |
| 5,404,222 | A | 4/1995 | Lis |
| 5,674,362 | A | 10/1997 | Underwood et al. |
| 5,764,362 | A | 6/1998 | Hill et al. |
| 6,501,550 | B1 | 12/2002 | Mihaljov |
| 7,268,888 | B2 * | 9/2007 | Hill ............................... 356/500 |
| 2008/0285051 | A1 * | 11/2008 | Hill ............................... 356/500 |

OTHER PUBLICATIONS

Jens Flügge, "Vergleichende Untersuchungen zur meβtechnischen Leistungsfähigkeit von Laserinterferometern and inkrementellen Maβstabmeβsystemen," Disserttion der Rheinisch-Westfälischen Technischen Hochschule Aachen (D82), Feb. 1996, p. 13-16.
M.E. Webber, et al., "In situ Combustion Measurements of $CO_2$ Using Diode Laser Sensors Near 2.0μm," *American Institute of Aeronautics and Astronautics Paper 2000-0075*, 38$^{th}$ Aerospace Sciences Meeting Exhibit Jan. 10-13, 2000.

(Continued)

*Primary Examiner* — Tarifur Chowdhury
*Assistant Examiner* — Jonathan Hansen
(74) *Attorney, Agent, or Firm* — Kenyon & Kenyon LLP

(57) ABSTRACT

In an interferometer system and a method for its operation, the interferometer system includes an interferometer having an interferometer light source whose emitted radiation is able to be split into a measuring arm and a reference arm, an object to be measured being disposed in the measuring arm, and the interferometer delivering interferometer signals as a function of the position of the object to be measured. In addition, a detecting device is provided for detecting fluctuations in the refractive index of the air in the measuring arm and/or reference arm. The detecting device includes a spectrometer unit; the spectrometer unit has at least one spectrometer light source, as well as at least one spectrometer detector unit. The bundles of rays emitted by the spectrometer light source are superimposed on the bundles of rays from the interferometer light source, the spectrometer light source emitting radiation having a wavelength which lies in the range of an absorption line of at least one specific air component. The spectrometer detector unit is used to generate spectrometer signals which characterize the absorption of the air component in terms of the spectrometer light-source wavelength in the measuring arm and/or reference arm.

35 Claims, 7 Drawing Sheets

OTHER PUBLICATIONS

Craig R. Schwarze et al., "Method for Obtaining Gas Concentration with a Phase-Based Metrology System," *Appl. Optics*, vol. 37, No. 18, pp. 3942-3947, 1998.

L.S. Rothman, et al., "The HITRAN an database,1986 Edition" *Appl. Optics* vol. 26, No. 19, pp. 4058-4097, 1987.

T. Fernholz, et al., "Digital, Phase-Sensitive Detection for in situ Diode-Laser Spectroscopy Under Rapidly Changing Transmission Conditions," *Appl. Phys. B*, 75, pp. 229-236, 2002.

Christopher S. Edwards, "Development of an IR Turntable Diode Laser Absorption Spectrometer for Trace Humidity Measurements at Atmospheric Pressure," *Appl. Optics*, vol. 38, No. 21, Jul. 20, 1999.

G. Boensch et al., "Measurement of the Refractive index of Air and Comparison with Modified Edlen's Formulae," *Metrologia*, vol. 35, pp. 133-139, Jan. 1998.

International Search Report, international PCT Application No. PCT/EP2008/008341, dated Jan. 15, 2009.

* cited by examiner

INTERFEROMETER SYSTEM AND METHOD FOR ITS OPERATION

FIELD OF THE INVENTION

The present invention relates to an interferometer system and a method for its operation.

BACKGROUND INFORMATION

When measuring length with the aid of interferometers, the wavelength of the laser radiation utilized in air is used as the measuring standard or material measure. Hereinafter, this is denoted as light wavelength. The light wavelength is dependent on specific ambient parameters like, for instance, the temperature, the pressure, the humidity and the precise gas composition. Therefore, knowledge of the correct light wavelength or compensation of environmental influences during the measurement is necessary for a correct measurement of length.

Laser interferometers, whose measuring path and/or reference path take(s) a course in air, are therefore subject to considerable measurement fluctuations which are caused by local fluctuations in the refractive index of the air. The stability, reproducibility and precision of such laser interferometers is thereby restricted to $1 \cdot 10^{-6}$ (workshop conditions) up to $1 \cdot 10^{-7}$ (good laboratory conditions) relative to the measuring path. Since the strongest fluctuations lie in the 0-10 Hz frequency range, they also adversely affect measurements which are performed in a relatively brief time. Therefore, today's demands on the stability and reproducibility of linear measurements in the electronics and semiconductor industry can no longer be satisfied. Typically, they lie in the range of $1 \cdot 10^{-8}$ to $1 \cdot 10^{-9}$ (i.e., 0.2 nm to 2 nm, given an average measuring distance of 20 cm) over time intervals of a few minutes.

A number of design approaches to detect and compensate for such fluctuations of refractive index in air have already been described.

In a first variant, the different ambient parameters such as air temperature, air pressure and air moisture are detected with the aid of suitable sensors, and a corrected or effective light wavelength is determined using what is called the Edlen formula. For instance, such a method is described in the dissertation by Jens Flügge, "Vergleichende Untersuchungen zur messtechnischen Leistungsfähigkeit von Laserinterferometern und inkrementellen Maβstabmesssystemen" ("Comparative Studies with Respect to the Metrological Performance of Laser Interferometers and Incremental Scale Measuring Systems"), RWTH Aachen (D82), February 1996, ISBN 3-89429-683-6, Pg. 13-14. The disadvantage in this procedure is that the various parameters with respect to the ambient conditions are determined only at discrete points and only in the vicinity of the optical measuring axis. The exact characteristic of these parameters along the measuring axis is therefore only approximately determined, resulting in turn in inaccuracies when determining the effective light wavelength, and therefore in the actual linear measurement. In addition, as a rule, the different sensors have significant response times, so that short-duration fluctuations of the parameters possibly occurring along the measuring axis are likewise not correctly measurable. Because of these shortcomings, the accuracy of this variant for sensing and compensating for fluctuations in the refractive index in the case of interferometric linear measurements in air must be regarded as limited.

A second variant provides for determining the air wavelength with the aid of a refractometer. Such a method is also described in the dissertation by Jens Flügge already mentioned above, "Vergleichende Untersuchungen zur messtechnischen Leistungsfähigkeit von Laserinterferometern und inkrementellen Maβstabmesssystemen" ("Comparative Studies with Respect to the Metrological Performance of Laser Interferometers and Incremental Scale Measuring Systems"), RWTH Aachen (D82), February 1996, ISBN 3-89429-683-6, Pg. 15-16. In principle, the same problems are apparent in this case as in the first variant; in addition, this procedure must be classified as relatively complicated and therefore costly.

U.S. Pat. No. 6,501,550 describes a third variant for correcting the light wavelength in interferometric measuring methods which provides an acousto-optical interferometer system for this purpose. With the aid of a sound transmitter and a sound receiver, the sound propagation time along the measuring axis is ascertained, and the sound velocity is determined by linking the measured sound propagation time to the position known via the optical interferometer measurement. Since in known manner, the sound velocity is in turn a function of the prevailing ambient conditions, an instantaneous average air temperature along the measuring axis may be determined via a suitable correction function. The air temperature determined in this manner is then used in turn as input variable for the method, already described at the outset, for determining the average light wavelength with the aid of the Edlen formula, etc. It must be cited as an advantage of this method that the sound velocity averaged along the measuring axis is used as a measured quantity going into the correction. Therefore, compensation may be made for any existing fluctuations in the temperature along the measuring axis, as well. However, the disadvantage in this case is that, because of the substantially greater wavelength of the sound wave (2-5 mm) and the stronger diffraction effects associated with it, the transverse expansion of the sound wave is 20-100 times greater than that of the light wave. This results in two crucial disadvantages of this method: First of all, sound reflections and deflections at adjacent machine parts, which can hardly be avoided, lead to interference signals which invalidate the measuring result of the ultrasonic measurement. Secondly, the ultrasonic wave covers a markedly greater volume of air around the measuring axis, so that air-temperature fluctuations outside of the light wave of the interferometer likewise result in measuring errors.

In a fourth variant, denoted hereinafter as multi-wavelength interferometry, the vacuum wavelength may be corrected by the use of a plurality of wavelengths. To this end, the dispersion behavior of air is used for the correction. With respect to methods of this kind, reference is made to U.S. Pat. No. 5,404,222 or to U.S. Pat. No. 5,764,362, for example, which describe corresponding procedures in detail. To be regarded as disadvantageous in the fourth variant of the environmentally compensated, interferometric measuring methods is the relatively large expenditure resulting for the necessary optical frequency multiplication of the highly accurate laser light source. Furthermore, a considerable measuring uncertainty in the case of the necessary determination of the dispersion behavior of air must always be taken into account, since the dispersion effect utilized is very small. Therefore, the measuring fluctuations are able to be reduced only slightly via this method.

SUMMARY

According to example embodiments of the present invention an interferometer system and a method for its operation are provided, via which improved measuring accuracy is ensured. In this context, the intention in particular is to detect any existing fluctuations of refractive index in air as precisely as possible, without great expenditure.

According to example embodiments of the present invention, it is provided to ascertain the fluctuations in the average refractive index of the air in the measuring arm and/or reference arm using a spectroscopic method. In so doing, the absorption of one air component along the measuring path and/or reference path of the interferometer system is determined metrologically using suitable detecting device(s), the absorption representing an indirect measure for the density or the average temperature of the respective air column based on the homogeneous air composition. The air columns covered coincide with the air columns of the interferometer system. The average refractive index detected via other detecting device(s) may be corrected suitably by the measured values regarding the absorption in brief time intervals. In this manner, fluctuations in the average refractive index of the air column, which are produced mainly by local temperature fluctuations, may therefore be offset. The measuring accuracy of the interferometer system described herein is able to be increased significantly compared to conventional methods.

The interferometer system includes an interferometer having an interferometer light source whose emitted radiation is able to be split into a measuring arm and a reference arm, an object to be measured being disposed in the measuring arm, and the interferometer delivering interferometer signals as a function of the position of the object to be measured. The interferometer system further includes a detecting device for detecting fluctuations in the refractive index of the air in the measuring arm and/or reference arm. The detecting device, in turn, include a spectrometer unit, the spectrometer unit having at least one spectrometer light source and a spectrometer detector unit. The bundles of rays from the interferometer light source are superimposed on the bundles of rays emitted by the one spectrometer light source; the spectrometer light source emits radiation having a wavelength which lies in the range of an absorption line of at least one specific air component. The spectrometer detector unit generates spectrometer signals which characterize the absorption of the air component in terms of the spectrometer light-source wavelength in the measuring arm and/or reference arm.

Furthermore, the detecting device may include a refractive-Index determination device which is used to determine the nominal refractive index $n(T_0, p_0, RH_0)$ of the air in the area of the measuring arm and/or reference arm.

In one possible variant, a first processor unit is provided, to which the spectrometer signals from the spectrometer unit are applied on the input side, the processor unit being designed to determine the fluctuations in the refractive index of the air in the measuring arm and or reference arm from the applied spectrometer signals, and to make corresponding output signals of the first processor unit available for further processing.

In this context, it is possible that, in addition, the output signals of the refractive-Index determination device are applied to the first processor unit, and the first processor unit is designed to determine the average refractive index in the area of the measuring arm and/or reference arm from the applied signals, and to make corresponding output signals of the first processor unit available for further processing.

It is further possible to provide a correction unit, applied to which on the input side are the output signals of the first processor unit with respect to the refractive index in the measuring arm and/or reference arm as well as the output signals of a second processor unit regarding the optical path-length difference which is determined by the second processor unit from the applied interferometer signals, the correction unit being designed to determine an effective refractive index from the output signals of the first processor unit with respect to the refractive index in the measuring arm and/or reference arm, and to process it in conjunction with the optical path-length difference, and to make corrected position signals with respect to the position of the object to be measured in the measuring arm available on the output side.

For example, the first processor unit may be designed to tune the wavelength of the spectrometer light source in the range of at least one absorption line of at least one air component whose absorption characteristic is determined.

Alternatively, however, the first processor unit may also be designed to tune a Fabry-Perot interferometer in the range of at least one absorption line of at least one air component whose absorption characteristic is determined, the Fabry-Perot interferometer being disposed on the side of the spectrometer detector unit.

In this context, the first processor unit may be designed to control a center wavelength of the tuning range of the spectrometer light source such that, or to tune the Fabry-Perot interferometer such that the center wavelength is at a fixed distance to the absorption peak of the air component whose absorption characteristic is determined.

For instance, it is also possible for the interferometer and the spectrometer unit to have one light source in common.

In the beam path of the spectrometer unit, optical elements may be disposed which direct the bundle of rays of the spectrometer light source multiple times along the measuring arm and/or reference arm of the interferometer.

The first processor unit may be designed to periodically tune the wavelength of the spectrometer light source in the tuning range, the tuning period being shorter in time than a typical fluctuation of the refractive index in the measuring arm and/or reference arm.

Preferably, the wavelength of the spectrometer light source lies in the range of at least one absorption line of at least one of the following air components: $N_2$, $O_2$, $CO_2$, $H_2O$.

In this context, the wavelength of the spectrometer light source advantageously lies at least in the range of an absorption line of water and a further air component.

It is further possible that a plurality of absorption lines having sharply different temperature coefficients of absorption are covered.

In one possible variant, the spectral width of the spectrometer light source is less than or comparable to the spectral width of the absorption line.

From the spectrometer signals applied on the input side, the first processor unit advantageously forms differential absorption values from the absorption in the center of the absorption line and the absorption in the periphery of the absorption line, which are then usable for determining the refractive index.

Moreover, it is possible for the first processor unit to determine the spectral width of the absorption line from the spectrometer signals applied on the input side.

For example, the interferometer has an interferometer detector unit having a plurality of interferometer detector elements for generating a plurality of position signals at various measuring points of the at least one object to be measured, and the spectrometer detector unit also includes a plurality of spectrometer detector elements for detecting the absorption of the air component in the associated measuring arm and/or reference arm.

In this context, the interferometer detector elements and the spectrometer detector elements may in each instance take the form of a detector array.

In addition, it is possible for the interferometer to take the form of a Michelson interferometer or a Fabry-Perot interferometer or a Fizeau interferometer or a Twyman-Green interferometer or a Speckle interferometer.

For example, the spectrometer detector unit may further include a tunable Fabry-Perot interferometer.

The spectrometer light source may preferably be in the form of a DFB laser or an external cavity laser.

The refractive-index determination device may include one or more sensors for determining air parameters and/or a reference interferometer having a known measuring distance for determining an average refractive index of the air in the measuring arm and/or reference arm.

In the method according to example embodiments of the present invention for operating an interferometer system, the latter includes an interferometer having an interferometer light source whose emitted radiation is split into a measuring arm and into a reference arm, an object to be measured being disposed in the measuring arm, and the interferometer delivering interferometer signals as a function of the position of the object to be measured. Furthermore, the fluctuations in the refractive index of the air in the measuring arm and/or reference arm are detected by a detecting device. In this context, the detecting device includes a spectrometer unit, a spectrometer light source emitting radiation having a wavelength which lies in the range of an absorption line of at least one air component, and the bundles of rays emitted by the spectrometer light source being superimposed on the bundles of rays from the interferometer light source. At least one spectrometer detector unit generates spectrometer signals which characterize the absorption of the air component in terms of the spectrometer light-source wavelength in the measuring arm and/or reference arm.

Furthermore, the detecting device may include refractive-Index determination device by which the nominal refractive index $n(T_0, p_0, RH_0)$ of the air in the area of the measuring arm and/or reference arm is determined.

In this context, the fluctuations in the refractive index of the air in the measuring arm and/or reference arm may be determined from the spectrometer signals, and corresponding signals may be made available for further processing.

For example, the average refractive index in the area of the measuring arm and/or reference arm may be determined, and corresponding signals may be made available for further processing.

It is possible to determine an effective refractive index from signals with respect to the refractive index in the measuring arm and/or reference arm, and to process this effective refractive index in conjunction with the optical path-length difference determined from the interferometer signals, and to make corrected position signals with respect to the position of the object to be measured in the measuring arm available for further processing.

In this context, the wavelength of the spectrometer light source may be tuned in the range of at least one absorption line of at least one air component whose absorption characteristic or dispersion characteristic is determined.

Furthermore, a Fabry-Perot interferometer may be tuned in the range of at least one absorption line of at least one air component whose absorption characteristic or dispersion characteristic is determined, the Fabry-Perot interferometer being disposed on the side of the spectrometer detector unit.

For instance, it is also possible to control the center wavelength of the tuning range of the spectrometer light source such that it is at a fixed distance to the absorption peak of the air component whose absorption characteristic or dispersion characteristic is determined.

In addition, it is possible to periodically tune the wavelength of the spectrometer light source in the tuning range, the tuning period being shorter in time than a typical fluctuation of the refractive index in the measuring arm and/or reference arm.

For instance, based on the spectrometer signals, differential absorption values may be formed from the absorption in the center of the absorption line and the absorption in the periphery of the absorption line, which are then used for determining the refractive index.

Moreover, the spectral width of the absorption line may be determined from the spectrometer signals.

Further features and aspects of example embodiments of the present invention are explained based on the following description with reference to the figures.

DETAILED DESCRIPTION

Figure 1:
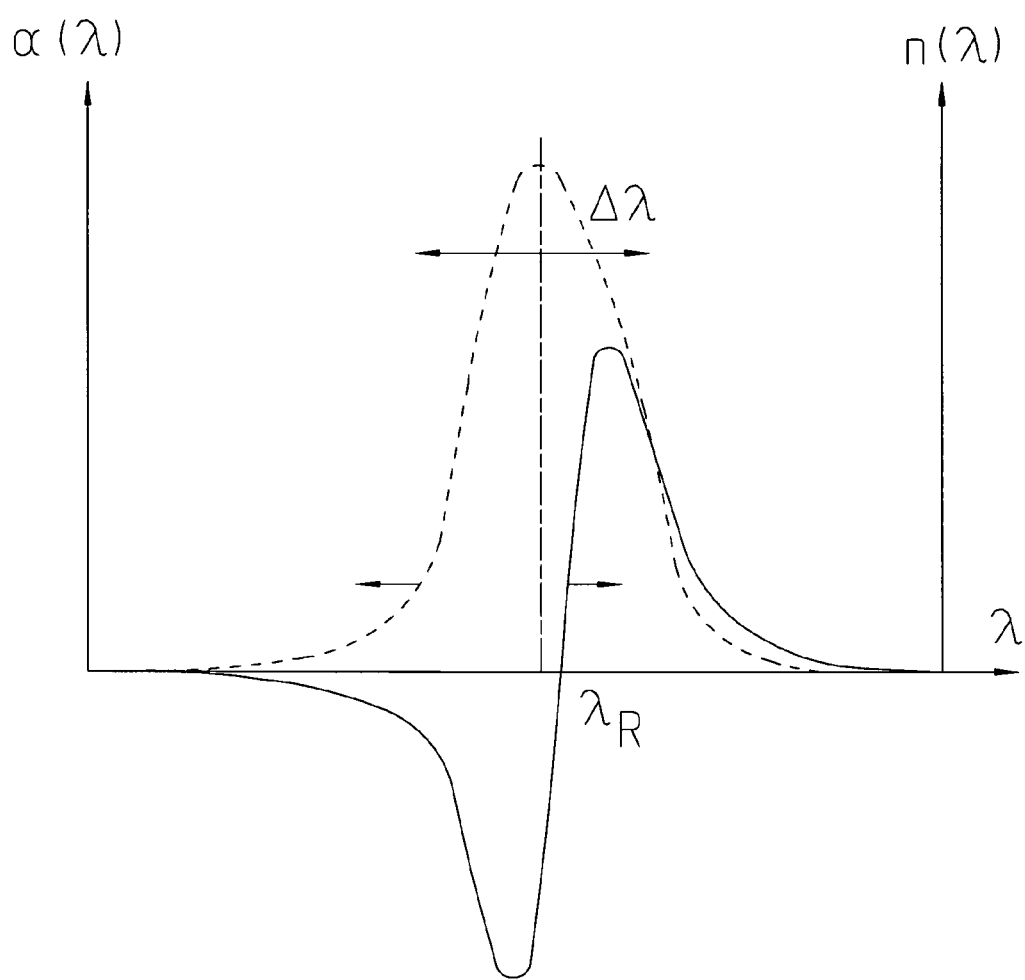
FIG. 1 shows a representation of the absorption and dispersion characteristic in the range of an absorption line.

Before the interferometer system according to example embodiments of the present invention are described based on the various drawings, the relevant theoretical fundamentals are first explained in the following.

Theoretical Fundamentals

Known interferometers measure the optical path-length difference OPD between a measuring distance MS and a reference distance RS. In so doing, the beam from a laser light source traverses measuring distance MS along measuring-beam path MSW and reference distance RS along reference-beam path RSW. In this connection, only air paths are taken into account, since usually the additional path lengths in optical components such as beam splitters and triple prisms in the measuring-beam path and reference-beam path, for example, are of equal length and are therefore compensated for. Therefore, the following applies:

$$OPD = \int_{MSW} n(x)dl - \int_{RSW} n(x)dl \qquad \text{(Eq. 1)}$$

At the output, the intention is for the interferometer to output a measured quantity, i.e., a measure for the geometrical path-length difference GPD=$L_{MSW}$−$L_{RSW}$ between length $L_{MSW}$ of measuring-beam path MSW and length $L_{RSW}$ of reference-beam path RSW. In order to be able to infer geometrical path-length difference GPD from optical path-length difference OPD, a correction factor $1/n_{eff}$ must therefore be determined where:

$$GPD = OPD/n_{eff} \quad \text{(Eq. 2)}$$

Effective refractive index $n_{eff}$ may be determined from average refractive indices $n_M$ and $n_R$ along beam paths MSW and RSW, respectively:

$$n_{eff} = \frac{OPD}{GPD} \quad \text{(Eq. 3)}$$
$$= n_M \cdot \frac{1}{1 - L_{RSW}/L_{MSW}} + n_R \cdot \frac{1}{1 - L_{MSW}/L_{RSW}}$$

where $$n_M = \frac{1}{L_{MSW}} \int_{MSW} n(x) dl \quad \text{(Eq. 4)}$$
$$n_R = \frac{1}{L_{RSW}} \int_{RSW} n(x) dl$$

In equations 3 and 4, it is sufficient to substitute estimated values for $L_{MSW}$ and $L_{RSW}$; for instance, the uncorrected or last-measured length values may be used.

The local refractive index n(x) of air is a function of the local parameters: air temperature T(x), air pressure p(x) and relative air humidity RH(x). This dependency may be linearized around a working point $T_0$, $p_0$, $RH_0$:

$$n(x) = n(T_0, p_0, RH_0) + \quad \text{(Eq. 5)}$$
$$\frac{\partial n}{\partial T}\bigg|_{T=T_0} \cdot (T(x) - T_0) + \frac{\partial n}{\partial p}\bigg|_{p=p_0} \cdot (p(x) - p_0) +$$
$$\frac{\partial n}{\partial RH}\bigg|_{RH=RH_0} \cdot (RH(x) - RH_0) =$$
$$n(T_0, p_0, RH_0) + \eta_T \cdot \Delta T(x) + \eta_p \cdot \Delta p(x) + \eta_{RH} \cdot \Delta RH(x)$$

where $$\eta_T = \frac{\partial n}{\partial T}\bigg|_{T=T_0} \quad \Delta T(x) = T(x) - T_0 \quad \text{(Eq. 6)}$$
$$\eta_p = \frac{\partial n}{\partial p}\bigg|_{p=p_0} \quad \Delta p(x) = p(x) - p_0$$
$$\eta_{RH} = \frac{\partial n}{\partial RH}\bigg|_{RH=RH_0} \quad \Delta RH(x) = RH(x) - RH_0$$

In this context, factors $\eta_T$, $\eta_p$ and $\eta_{RH}$ are as a rule slightly dependent on the air composition.

Nominal refractive index $n(T_0, p_0, RH_0)$ at working point $T_0$, $p_0$, $RH_0$ may be determined using the familiar Edlen formula if the working point is defined by corresponding measured values of assigned environmental sensors. Deviations of local air parameters $\Delta T(x)$, $\Delta p(x)$ and $\Delta RH(x)$ along beam paths MSW and RSW lead to fluctuations of average refractive indices $n_M$ and $n_R$ about nominal value $n(T_0, p_0, RH_0)$. Mainly local temperature fluctuations $\Delta T(x)$ are relevant in practice. The pressure fluctuations are distributed homogeneously over the measuring volume due to the rapid pressure equalization in air. Air pressure $p_0$ measured remotely from beam paths MSW and RSW therefore corresponds substantially to air pressure p(x) along the beam paths. The analogous holds true for relative air humidity RH, as well. It may be formulated with high accuracy:

$$\Delta p(x) \approx 0 \; p(x) \approx p_0$$

$$\Delta RH(x) \approx 0 \; \text{or} \; RH(x) = RH_0 \quad \text{(Eq. 7)}$$

The only location dependency of the refractive index therefore comes about through the local temperature influence. This also holds true for other parameters which are influenced by the air. Equation 5 is therefore reduced to:

$$n(x) = n(T_0, p_0, RH_0) + \eta_T \cdot \Delta T(x) \quad \text{(Eq. 8)}$$

and with equation 4, yields:

$$n_M = n(T_0, p_0, RH_0) + \frac{\eta_T}{L_{MSW}} \int_{MSW} \Delta T(x) dl \quad \text{(Eq. 9)}$$
$$= n(T_0, p_0, RH_0) + \eta_T \cdot \Delta T_{MSW}$$
$$n_R = n(T_0, p_0, RH_0) + \frac{\eta_T}{L_{RSW}} \int_{RSW} \Delta T(x) dl$$
$$= n(T_0, p_0, RH_0) + \eta_T \cdot \Delta T_{RSW}$$

Average temperature deviations $\Delta T_{MSW}$ and $\Delta T_{RSW}$ represent mean values over the two beam paths MSW and RSW, respectively. Coefficient $\eta_T$ may be determined by derivation of the Edlen formula, and lies at approximately $1 \cdot 10^{-6} K^{-1}$.

An essential prerequisite for the applicability of this relation is the constant composition of the air. That is why, for example, there must be no gas sources such as nitrogen rinsings, protective-gas feeds or combustion processes in the vicinity of the interferometer. They would alter the gas composition locally, and therefore interfere with an important prerequisite with respect to Equation 8. If such gas sources cannot be avoided, the beam paths of the laser interferometer must be shielded well. A further alternative to this is described further below.

According to example embodiments of the present invention, average air-temperature deviations $\Delta T_{MSW}$ and $\Delta T_{RSW}$ along beam paths MSW and RSW are determined indirectly by optical absorption spectroscopy in respect to individual air components (molecules) with the aid of a spectrometer unit. In so doing, it is best to select a main component of the air such as $N_2$, $O_2$, $CO_2$ or $H_2O$ for the spectroscopy. Hereinafter, the air component selected is denoted by the index $\epsilon$. The selection is made by a suitable choice of the wavelength $\lambda_S$ of the light source of the spectrometer unit close to an absorbing molecular resonance of air component $\epsilon$. Transmissions $TR_{\epsilon,M}(\lambda_S)$ and $TR_{\epsilon,R}(\lambda_S)$ through the air columns of beam paths MSW and RSW are given by:

$$TR_{\epsilon,M}(\lambda_S) = \exp\left(-\int_{MSW} \alpha_\epsilon(\lambda_S, x) dl\right) \quad \text{(Eq. 10)}$$
$$TR_{\epsilon,R}(\lambda_S) = \exp\left(-\int_{RSW} \alpha_\epsilon(\lambda_S, x) dl\right)$$

where $\alpha_\epsilon(\lambda_S, x)$ denotes the absorption coefficient, given wavelength $\lambda_S$ at location x. This absorption coefficient $\alpha_\epsilon(\lambda_S, x)$ is a function of pressure p, temperature T, relative air humidity RH and normalized, spectral line distribution $\psi_\epsilon(\lambda_S, T, p, RH)$. The latter, in turn, is a function of air parameters T, p and RH:

$$\alpha_\varepsilon(\lambda_S, x) = g_\varepsilon(T, p, RH) \cdot \Psi_\varepsilon(\lambda_S, T, p, RH) \quad \text{(Eq. 11)}$$
$$= g_\varepsilon(T(x), p_0, RH_0) \cdot \Psi_\varepsilon(\lambda_S, T(x), p_0, RH_0)$$

with normalization over absorption line $A_\epsilon$:

$$\int_{A_\varepsilon} \Psi_\varepsilon(\lambda_S, T(x), p_0, RH_0) d\lambda_S = 1 \quad \text{(Eq. 12)}$$

Function $g_\epsilon$ essentially includes the proportional influence of density $\rho_\epsilon$ of air component $\epsilon$ and the temperature-dependent population density $\sigma_\epsilon(T)$ of the initial state of absorption line $A_\epsilon$ (see M. E. Webber et al., "In situ Combustion Measurements of $CO_2$ Using Diode Laser Sensors Near 2.0 μm", American Institute of Aeronautics and Astronautics Paper 2000-0775).

Given an ideal gas having density p and a relative constituent $r_\epsilon$ of air component $\epsilon$ in respect of the total air, the following applies:

$$\rho_\varepsilon = r_\varepsilon \cdot \rho = r_\varepsilon \cdot \frac{p}{R \cdot T}, \quad \text{(Eq. 13)}$$

where R denotes the Rydberg constant. Upon proper examination, relative constituent $r_\epsilon$ is a function of relative air humidity RH, as well as of temperature T.

For population density $\sigma_\epsilon(T)$, the following applies in the thermal equilibrium:

$$\sigma_\varepsilon(T) = \frac{e^{-E_\varepsilon/kT}}{\sum_n e^{-E_n/kT}}, \quad \text{(Eq. 14)}$$

where $E_n$ denotes the energy of state n of the selected molecule, $E_\epsilon$ denotes the energy of the initial state of selected absorption line $A_\epsilon$ and k denotes the Boltzmann constant.

Resulting from this is a complex temperature dependency of function $g_\epsilon$:

$$g_\varepsilon(T, p, RH) \propto r_\varepsilon(T, RH) \cdot \frac{p}{T} \cdot \frac{e^{-E_\varepsilon/kT}}{\sum_n e^{-E_n/kT}} \quad \text{(Eq. 15)}$$

Spectral line distribution $\psi_\epsilon(\lambda_S, T, p, RH)$ includes various shares, as well. First of all, the thermal movement of the molecules leads to a temperature-dependent Doppler widening of the absorption line. On the other hand, air pressure p influences the number of collisions between the molecules, so that what is termed a pressure broadening comes about.

Depending upon whether absorption coefficient $\alpha_\epsilon(\lambda_S, x)$ is determined at a defined wavelength $\lambda_S$ (hereinafter: "spectrally selective case") or is integrated spectrally over absorption line $A_\epsilon$ (hereinafter: "spectrally integrated case"), different linearizations may be performed with respect to location-dependent temperature T(x):

$$\alpha_\varepsilon(\lambda_S, x) = \alpha_{\varepsilon 0} + \gamma_\varepsilon \cdot \Delta T(x) \quad \text{(Eq. 16)}$$
$$\int_{A_\varepsilon} \alpha_\varepsilon(\lambda_S, x) d\lambda_S = \alpha'_{\varepsilon 0} + \gamma'_\varepsilon \cdot \Delta T(x),$$

where in general, $\alpha_{\epsilon 0}$, $\gamma_\epsilon$ and $\alpha'_\epsilon$, $\gamma'_\epsilon$ are a function of $\lambda_S$, $T_0$, $p_0$ and $RH_0$. In the spectrally selective case, it is advantageous to select wavelength $\lambda_S$ in the center of the absorption line.

Equations 10 and 16 allow the determination, according to example embodiments of the present invention, of average air-temperature deviations $\Delta T_{MSW}$ and $\Delta T_{RSW}$ along beam paths MSW and RSW for the spectrally selective case:

$$\Delta T_{MSW} = -\frac{1}{\gamma_\varepsilon \cdot L_{MSW}} \cdot \ln(TR_{\varepsilon,M}(\lambda_S)) - \frac{\alpha_{\varepsilon 0}}{\gamma_\varepsilon} \quad \text{(Eq. 17a)}$$
$$\Delta T_{RSW} = -\frac{1}{\gamma_\varepsilon \cdot L_{RSW}} \ln(TR_{\varepsilon,R}(\lambda_S)) - \frac{\alpha_{\varepsilon 0}}{\gamma_\varepsilon}$$

and for the spectrally integrated case:

$$\Delta T_{MSW} = -\frac{1}{\gamma'_\varepsilon \cdot L_{MSW}} \cdot \int_{A_\varepsilon} \ln(TR_{\varepsilon,M}(\lambda_S)) d\lambda_S - \frac{\alpha'_{\varepsilon 0}}{\gamma'_\varepsilon} \quad \text{(Eq. 17b)}$$
$$\Delta T_{RSW} = -\frac{1}{\gamma'_\varepsilon \cdot L_{RSW}} \cdot \int_{A_\varepsilon} \ln(TR_{\varepsilon,R}(\lambda_S)) d\lambda_S - \frac{\alpha'_{\varepsilon 0}}{\gamma'_\varepsilon}$$

A composite may be made of equations 9 and 17, for the spectrally selective case:

$$n_M = n(T_0, p_0, RH_0) - \beta_\varepsilon \cdot \left[\frac{1}{L_{MSW}} \cdot \ln(TR_{\varepsilon,M}(\lambda_S)) + \alpha_{\varepsilon 0}\right] \quad \text{(Eq. 18a)}$$
$$n_R = n(T_0, p_0, RH_0) - \beta_\varepsilon \cdot \left[\frac{1}{L_{RSW}} \cdot \ln(TR_{\varepsilon,R}(\lambda_S)) + \alpha_{\varepsilon 0}\right]$$

and the spectrally integrated case:

$$n_M = \quad \text{(Eq. 18b)}$$
$$n(T_0, p_0, RH_0) - \beta'_\varepsilon \cdot \left[\frac{1}{L_{MSW}} \cdot \int_{A_\varepsilon} \ln(TR_{\varepsilon,M}(\lambda_S)) d\lambda_S + \alpha'_{\varepsilon 0}\right]$$
$$n_R =$$
$$n(T_0, p_0, RH_0) - \beta'_\varepsilon \cdot \left[\frac{1}{L_{RSW}} \cdot \int_{A_\varepsilon} \ln(TR_{\varepsilon,R}(\lambda_S)) d\lambda_S + \alpha'_{\varepsilon 0}\right]$$

with $$\beta_\varepsilon = \frac{\eta_T}{\gamma_\varepsilon} \text{ and } \beta'_\varepsilon = \frac{\eta_T}{\gamma'_\varepsilon}.$$

In general, coefficients $\alpha_{\epsilon 0}$, $\beta_\epsilon$ and $\alpha'_{\epsilon 0}$, $\beta'_\epsilon$, respectively, are a function of nominal air parameters $T_0$, $p_0$, $RH_0$. That is why, in the case of very high accuracy requirements, these dependencies must be determined at least once. The nominal air parameters may be measured continuously by the environmental sensors. Alternatively, coefficients $\alpha_{\epsilon 0}$, $\beta_\epsilon$ and $\alpha'_{\epsilon 0}$, $\beta'_\epsilon$, respectively, may also be determined by an additional calibration interferometer using spectroscopic absorption measurement. Since the lengths of the air paths in the calibration interferometer are known, coefficients $\alpha_{\epsilon 0}$, $\beta_\epsilon$ and $\alpha'_{\epsilon 0}$, $\beta'_\epsilon$ may be derived by a balancing calculation with the aid of Equations 2, 3 and 18.

Hereinafter, the first term n $(T_0, p0, RH_0)$ from Equations 18a and 18b, respectively, is denoted as nominal refractive index, the second term as refractive-index fluctuation. The two terms in sum yield average refractive index $n_M$ and $n_R$, respectively.

Equations 2, 3 and 18 form the basis for the compensation, according to example embodiments of the present invention, of the refractive-index fluctuations of air with the aid of the measurement of transmissions $T_{\epsilon,M}$ and $T_{\epsilon,R}$ in the range of an absorption line.

In addition to the spectrally selective and the spectrally integrated case, further parameters derived from the transmission values may also be utilized. Thus, for example, it is also possible to determine the spectral width of the absorption line which, as described above, is likewise a function of the air temperature. The refractive index is then determined in a manner analogous to Equations 18a and 18b.

The equations above imply that the spectroscopically determined, average air-temperature deviations $\Delta T_{MSW}$ and $\Delta T_{RSW}$ cover the same air columns as those which are transilluminated by the interferometer. Therefore, both for measuring-beam path MSW and for reference-beam path RSW, preferably the laser beam of the spectrometer unit must travel in as collinear or anti-collinear fashion as possible with respect to the bundle of rays of the interferometer. Moreover, the beam cross-sections or the beam profiles of the light sources of the interferometer and of the spectrometer unit should be identical, in order to permit the same transverse weighting of the air-temperature distributions.

In the case of the frequently utilized interferometers whose reference-beam path RSW travels completely or almost completely in glass, the determination of refractive index $n_R$ may be omitted, and instead of Equation 3, the following applies:

$$n_{eff} = n_M \quad \text{(Eq. 19)}$$

In principle, electronic, vibronic or rotary transitions of the molecules are suitable as molecular resonances, so long as they have a sufficiently absorbent effect optically. As a rule, electronic transitions lie in the UV range at $\lambda_S < 400$ nm, and are able to be measured by UV laser diodes available today (possibly with frequency doubling or frequency tripling). The formulas above are reduced somewhat by the low temperature dependency of the population density of the initial state (=original state). Preferably, the weak absorption lines are suitable as favorable molecular resonances in the UV range, since generally the absorption lines are more likely too strong. Alternatively, in the case of a strong molecular resonance in the UV range, wavelength $\lambda_S$ in the edge area of the line may be selected, accompanied by transmission that is still sufficient.

However, vibronic transitions are especially advantageous, since they lie in the easily accessible, red or near infrared spectral range, and suitable, narrow-band and cost-effective light sources are available as spectrometer light sources. For example, they are DFB laser diodes, VCSELs or laser diodes with external cavity in the spectral range $\lambda_S = 0.5 \mu m \ldots 10 \mu m$. Typical line widths of DFB lasers lie below 10 MHz, while the line widths of typical vibronic molecular transitions, given normal air conditions, lie in the 3 GHz range, and are therefore markedly greater than those of the laser. This is advantageous, since the absorption effects detected thereby become particularly clear.

In general, rotation transitions may be measured with the aid of quantum cascade laser diodes in the $\lambda_S > 10 \mu m$ wavelength range.

The device of example embodiments of the present invention and the method of example embodiments of the present invention may be further improved by measuring a plurality of absorption lines. These measurements should be acquired separately and, for example, may be performed one after another in time by an expanded tuning of the spectroscopy light source. The further measured absorption lines may relate to the same air component $\epsilon$ or to different air components $\epsilon_1, \epsilon_2, \epsilon_3, \ldots$. For instance, the variation in the air composition may be corrected by the additional information. In this context, in is particularly advantageous to directly measure the water vapor $(H_2O)$ in addition to a second air component, since this air component brings about the greatest fluctuations in the air composition. In applications in which gases must be introduced, these gas concentrations may likewise be measured directly by associated absorption lines. It is then no longer necessary to shield these gas sources from the interferometer beam path.

According to the Kramers-Kronig relation, associated with each absorption line of a molecular transition is also a dispersion characteristic, i.e., a change in the refractive index $n(\lambda)$ in the range of a molecular resonance at $\lambda = \lambda_R$; for this, reference is made, for instance, to FIG. 1. This dispersion characteristic exhibits a negative slope (anomalous dispersion) within spectral width $\Delta\lambda$, of the absorption line. Absorption measurements and dispersion measurements supply similar information which may be converted into each other by the Kramers-Kronig relation (see "Method for obtaining gas concentration with a phase-based metrology system", Craig R. Schwarze et. al., Appl. Optics 37, No. 18, 3942-3947, 1998). However, dispersion effects are substantially weaker in practice, and therefore more difficult to detect than the absorption effects. Thus, it is apparent from a simple atomic vibration model that maximum refractive-index change $\Delta n_{MAX}$ and maximum absorption $\Delta\alpha_{MAX}$ within the resonance are related as follows:

$$\Delta n_{MAX} \approx \frac{\lambda}{2\pi} \cdot \Delta\alpha_{MAX} \quad \text{(Eq. 20)}$$

For a typical vibronic transition with $\Delta\alpha_{MAX} \sim 0.01$ m$^{-1}$ given $\lambda \sim 600$ nm, $\Delta n_{MAX} \sim 10^{-9}$ is obtained. This corresponds to an ostensible change of length in an interferometer of only 1 nm per meter measuring distance, which can hardly be detected in practice. On the other hand, an associated absorption of 1% per meter measuring distance is able to be verified easily and with high accuracy. These assessments show the special advantage of an absorption measurement in comparison to a dispersion measurement.

Next, after these theoretical discussions, interferometer systems according to example embodiments of the present invention, as well as methods for their operation are now explained.

First Exemplary Embodiment

Figure 2A:
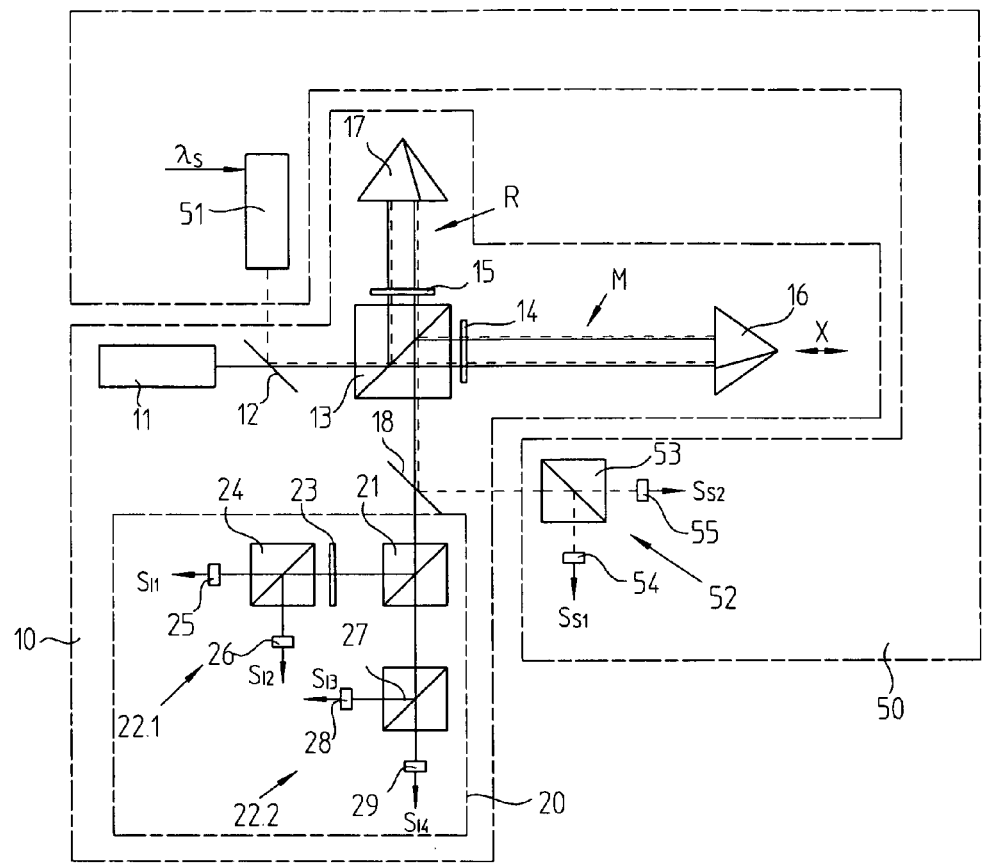
FIG. 2*a* shows a schematic representation of an interferometer system according to an example embodiment of the present invention.
Figure 2B:
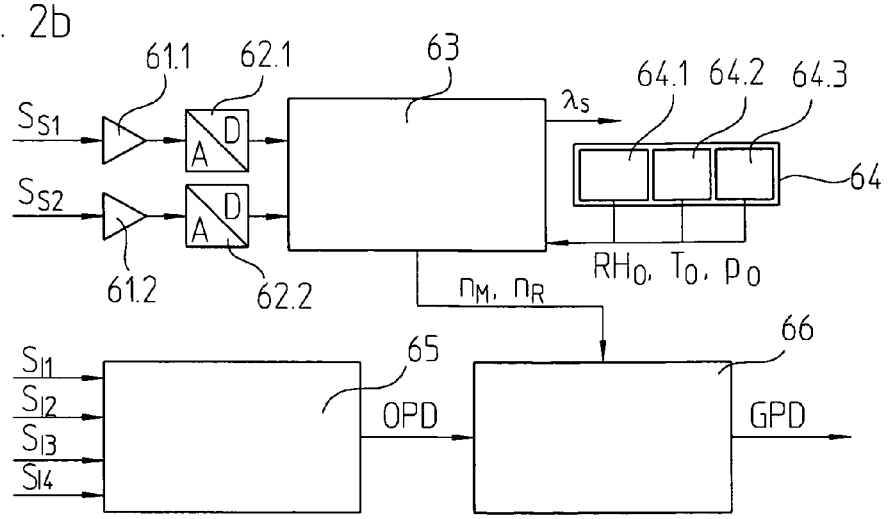
FIG. 2*b* shows a schematic representation for clarifying the signal processing of the interferometer system illustrated in FIG. 2*a*.

A first exemplary embodiment of the interferometer system is shown in schematized fashion in FIGS. 2a and 2b. FIG. 2a shows the beam path itself; FIG. 2b illustrates the associated signal processing.

For example, the interferometer system may be used for the extremely precise determination of the position of an object to be measured that is displaceable in one or more measuring directions. For instance, suitable applications to this end are in the manufacturing of semiconductors when, for example, the position of the table of a wafer stepper is to be determined. Alternatively, however, the interferometer system may also be used for the extremely precise sensing of the topography of an object to be measured. In this case, the position is determined in terms of the surface of an object to be measured that is situated in the measuring arm.

A interferometer 10 as well as a spectrometer unit 50 of the interferometer system are shown in the example of FIG. 2a; various signal-processing components are shown in FIG. 2b.

In this example embodiment, interferometer 10 includes an interferometer light source 11, for instance, a suitable laser that emits a linearly polarized bundle of rays having wavelength $\lambda_I$; for example, wavelength $\lambda_I$ may be selected at $\lambda_I$=500 nm 1500 nm; especially preferred wavelengths would be about $\lambda_I$=633 nm or $\lambda_I$=532 nm. In FIG. 2a, as in the figures to be described in the following, as well, the beam path of interferometer 10 to be explained is drawn in with a solid line. After passing through a first beam-splitter element 12, the bundle of rays emitted by interferometer light source 11 strikes a first interferometer beam-splitter element 13, where the bundle of rays is split into two partial bundles of rays that are fed to a measuring arm M and a reference arm R of interferometer 10. First beam-splitter element 12 takes the form of a dichroic beam splitter; first interferometer beam-splitter element 13 is in the form of a familiar polarizing beam-splitter cube.

In measuring arm and reference arm M, R, the partial bundles of rays pass through $\lambda$/4-plates 14, 15, respectively, before they strike retroreflector elements 16, 17, from which they are reflected back again in the direction of interferometer beam-splitter element 13. Retroreflector elements 16, 17 in this example are in the form of well-known triple prisms.

Retroreflector element 17 in reference arm R of interferometer 10 is stationary, whereas in this exemplary embodiment, retroreflector element 16 in measuring arm M of interferometer 10 is disposed—together with an object to be measured (not shown) whose position is to be determined—in a manner allowing movement in the indicated x-direction (measuring direction).

After the repeated passage of the partial bundles of rays reflected back by retroreflector elements 16, 17, they pass through respective $\lambda$/4-plates 14, 15 again and are finally superimposed with the aid of first interferometer beam-splitter element 13. The superimposed partial bundles of rays subsequently pass through a second dichroic beam-splitter element 18 before they propagate in the direction of an interferometer detector unit 20.

In interferometer detector unit 20, a second interferometer beam-splitter element 21 is provided in the form of a neutral beam-splitter cube, via which the pair of partial bundles of rays is split in the direction of two detector configurations 22.1, 22.2.

First detector configuration 22.1 includes a further $\lambda$/4-plate 23, a third interferometer beam-splitter element 24 taking the form of a polarizing beam-splitter cube, as well as two downstream interferometer detector elements 25, 26. Interferometer signals $S_{I1}$, $S_{I2}$ result at the outputs of the two interferometer detector elements 25, 26.

Second detector configuration 22.2 includes a fourth interferometer beam-splitter element 27, again in the form of a polarizing beam-splitter cube, as well as two downstream interferometer detector elements 28, 29. Further interferometer signals $S_{I3}$, $S_{I4}$ result at the outputs of the two interferometer detector elements 28, 29. Detector elements 25, 26, 28, 29 are preferably in the form of a detector array.

Viewed in the beam direction, the polarization axes of the two polarizing interferometer beam-splitter elements 24 and 27 are tilted (in a manner not shown) by 45° with respect to the polarization axis of polarizing interferometer beam-splitter element 13. The two partial bundles of rays of measuring arm M and of reference arm R are thereby brought into interference.

Interferometer signals $S_{I1}$, $S_{I2}$, $S_{I3}$, $S_{I4}$ generated by interferometer detector elements 25, 26, 28, 29 are subsequently evaluated in known manner in order to generate a measured quantity with respect to the optical path-length difference OPD of interest in interferometer 10, which represents a measure for the position of the object to be measured.

The variant of interferometer 10 shown in FIG. 2a, including the signal processing used in this case, corresponds to conventional interferometers. In principle, both homodyne and heterodyne methods may be used for the operation and for the evaluation.

The utilization and the form of the detecting device which is used for detecting fluctuations in the refractive index of the air in measuring arm and/or reference arm M, R of interferometer 10 are decisive. Thus, according to example embodiments of the present invention, to this end a spectrometer unit 50 is used as suitable detecting device whose structure and integration into interferometer 10 is explained below; the beam path of the bundles of rays determinative for the functioning of spectrometer unit 50 is drawn in with a dotted line in FIG. 2a.

Spectrometer unit 50 includes a spectrometer light source 51, likewise taking the form of a laser, which emits a linearly polarized bundle of rays having wavelength $\lambda_S$. In this context, wavelength $\lambda_S$ of the radiation emitted by spectrometer light source 51 is selected according to the theoretical considerations above, so that it lies in the range of an absorption line of at least one air component c. For example, it may be an absorption line of water at 723.5 nm or an absorption line of oxygen at 761 nm; in this case, spectrometer light source 51 then emits radiation at 723.5 nm or 761 nm, as well. In principle, it is also considered to select the wavelength of the spectrometer light source in the range of at least one absorption line of air components $N_2$, $O_2$, $CO_2$, etc. A comprehensive compilation of absorption lines of air components is found in "The HITRAN database: 1986 edition", L. S. Rothman et al., Appl. Opt. 26 No. 19 (1987), 4058-4097.

Moreover, it proves to be advantageous to measure a plurality of absorption lines having sharply different temperature coefficients of the absorption; in the same manner, it is best if the spectral width of the respective spectrometer light source is comparable to or less than the spectral width of the respective absorption line.

The temperature dependency and current dependency of the wavelength of laser diodes are used advantageously to adjust and modulate the wavelength of spectrometer light source 51. For instance, the temperature may be regulated by a Peltier element on which the laser diode is mounted. The wavelength is adjusted coarsely by a suitable selection of the operating temperature of the laser diode. The fine adjustment and, if applicable, also a rapid modulation are achieved by a suitable, if necessary, modulated operating current. Alternative possibilities for adjusting and modulating wavelength are provided by external cavity laser diodes or laser diodes having downstream optical modulators.

The bundle of rays emitted by spectrometer light source 51 is deflected by 90° via first beam-splitter element 12 and in this manner is superimposed in collinear fashion on the bundle of rays of interferometer light source 11. As in the interferometer beam path, the bundle of rays from spectrometer light source 51 is subsequently split via first interferometer beam-splitter element 13. In measuring arm and reference arm M, R, the partial bundles of rays of spectrometer light source 51 likewise pass through λ/4-plates 14, 15 before they strike retroreflector elements 16, 17, from which they are reflected back again in the direction of interferometer beam-splitter element 13. After passing through λ/4-plates 14, 15 once more, the partial bundles of rays from spectrometer light source 51 finally arrive again at first interferometer beam-splitter element 13, where they are superimposed to form a superimposed pair of partial bundles of rays which, like the partial bundles of rays of interferometer light source 11, further propagate in the direction of second beam-splitter element 18. Via second beam-splitter element 18, the partial bundles of rays of spectrometer light source 51 are split off from those of interferometer light source 11 and subsequently propagate in the direction of a spectrometer detector unit 52. In spectrometer detector unit 52, the partial bundles of rays initially reach a spectrometer beam-splitter element 53 in the form of a polarizing beam-splitter cube. There, the incident bundle of rays is split into two partial bundles of rays, which subsequently propagate in the direction of two downstream spectrometer detector elements 54, 55. The partial bundle of rays which previously passed through measuring arm M of interferometer 10 is detected by first spectrometer detector element 54; the partial bundle of rays which previously passed through reference arm R of interferometer 10 is detected by second spectrometer detector element 55. In contrast to third and fourth interferometer beam-splitter elements 24, 27, spectrometer beam-splitter element 53 is designed or oriented such that no interference of the partial bundles of rays from measuring arm and reference arm M, R results. Therefore, via spectrometer detector elements 54, 55, spectrometer signals $S_{S1}$, $S_{S2}$ are acquired which in each case represent an absorption signal with respect to the path traversed in measuring arm and reference arm M, R; spectrometer detector elements 54, 55 may take the form of a detector array. Specifically, in the present example, spectrometer signals $S_{S1}$, $S_{S2}$ are generated which characterize the absorption of one air component c in terms of spectrometer light-source wavelength $\lambda_S$ in measuring arm and/or reference arm M, R.

First interferometer beam-splitter element 13, as well as the two λ/4-plates 14, 15 in the measuring arm and reference arm of the interferometer are traversed by the partial bundles of rays of interferometer light source 11 as well as of spectrometer light source 51. Therefore, these components must satisfy their respective polarization optical properties in the case of both wavelengths $\lambda_I$ and $\lambda_S$. A special optimization of the corresponding layers of these components acting in polarizing optical fashion is therefore necessary. In doing so, it proves to be advantageous for this optimization if the two wavelengths $\lambda_I$ and $\lambda_S$ are chosen to be closely adjacent to one another.

In the following, an example for the processing of the various signals $S_{I1}$, $S_{I2}$, $S_{I3}$, $S_{I4}$, $S_{S1}$, $S_{S2}$ of interferometer 10 and of spectrometer unit 50 in the interferometer system according to example embodiment of the present invention is now explained with reference to FIG. 2b.

As apparent from FIG. 2b, after amplification by amplifier elements 61.1, 61.2 and digitizing by A/D-converter elements 62.1, 62.2, spectrometer signals $S_{S1}$, $S_{S2}$ are fed to a first processor unit 63.

In addition, first processor unit 63 controls wavelength $\lambda_S$ of spectrometer light source 51 and tunes it in the range of the at least one absorption line of the at least one air component ε whose absorption characteristic is determined. Preferably, the center wavelength of the tuning range is selected such that it corresponds with the absorption peak of corresponding air component ε or is at a fixed distance to it. In this connection, the cycle time for such a tuning process should be selected to be as short as possible; values in the range of 10 msec to 1 μsec prove to be advantageous. Moreover, at the same time, the measurement of transmissions $T_{\epsilon,M}(\lambda_S)$ and $T_{\epsilon,M}(\lambda_S)$ in measuring arm and reference arm M, R is performed.

Since the signal levels of spectrometer signals $S_{S1}$, $S_{S2}$ are a function not only of the absorption in air, but also of the reflection and transmission properties, respectively, as well as the positional tolerance and form tolerance of all component parts of the interferometer, these unwanted portions of the signal should be corrected to the greatest extent possible. To that end, during the process of tuning wavelength $\lambda_S$, spectrometer signals $S_{S1}$, $S_{S2}$ are determined in the absorption peak of air component ε and outside of the absorption line, and the difference is formed. This difference is a function only of the absorption of air component ε and the optical performance of spectrometer light source 51. The latter is either stabilized in a manner not shown or likewise measured and offset accordingly.

In addition to spectrometer signals $S_{S1}$, $S_{S2}$, output signals $RH_0$, $T_0$, $p_0$ of schematically indicated refractive-Index determination device 64 are also applied to first processor unit 63 in this exemplary embodiment. Refractive-index determination device 64 in this exemplary embodiment likewise belongs to the detecting device, mentioned above, for detecting the refractive-index fluctuations, and are used specifically to ascertain the average refractive index of the air in the area of measuring arm and/or reference arm M, R. Refractive-index determination device 64 may include a plurality of sensors 64.1, 64.2, 64.3 which deliver nominal measured values for relative air humidity RH, air temperature T and air pressure p in the area of measuring arm and/or reference arm M, R to first processor unit 63.

In the present example, based on the signals of refractive-index determination means 64 and spectrometer signals $S_{S1}$, $S_{S2}$, first processor unit 63 determines the values for local refractive indices $n_M$ and $n_R$ in measuring arm and reference arm M, R using Equations 18a, 18b specified above in the theory section. The values for $n_M$ and $n_R$ thus ascertained are made available as output signals of first processor unit 63 to a downstream correction unit 66 for further processing.

As an alternative, first processor unit 63 may also be designed such that the fluctuations in refractive index $n_M$, $n_R$ of the air in measuring arm and/or reference arm M, R may be determined from spectrometer signals $S_{S1}$, $S_{S2}$ applied on the input side, and corresponding output signals are made available for further processing. In principle, evaluation of output signals from refractive-index determination device is not necessary in such a variant.

As likewise evident from FIG. 2b, in the present example, interferometer signals $S_{I1}$, $S_{I2}$, $S_{I3}$, $S_{I4}$ are fed to a second processor unit 65 which, in well-known manner, determines optical path-length difference OPD and makes it available as output signal to correction unit 66 for further processing, as well.

Correction unit 66 is designed such that, by way of the signals regarding refractive indices $n_M$ and $n_R$ applied on the input side, first of all an effective refractive index $n_{\text{eff}}$ for measuring arm and/or reference arm M, R may be determined according to Equation 3, to then process it in conjunction with the interferometer signals or interferometer signals $S_{I3}$, $S_{I4}$, $S_{S1}$, $S_{S2}$, prepared corresponding to optical path-length difference OPD, such that according to Equation 2 geometrical path-length difference GPD of interest as measured quantity or corrected position signals regarding the position of the object to be measured in measuring arm M result on the output side.

As an alternative to the direct tuning of wavelength $\lambda_S$ of a narrow-band spectrometer light source 51, it would also be possible to provide a broadband spectrometer light source 51 whose spectral expansion overlaps the at least one absorption line of the at least one air component c. In this case, a Fabry-Perot interferometer must be disposed directly in front of beam-splitter element 53 in FIG. 2a. This interferometer is tuned via first processor unit 63 in the range of the at least one absorption line of the at least one air component ϵ whose absorption characteristic is determined.

In this context, the tuning range of the spectrometer light source may be controlled or the Fabry-Perot interferometer may be tuned such that the respective center wavelength is at a fixed distance to the absorption peak of that air component ϵ whose absorption characteristic is determined.

Processor units 63, 65 as well as correction unit 66 shown in FIG. 2b may be implemented in any manner desired in software and/or hardware, that is, the separation of the various components illustrated in FIG. 2b is used merely to simplify the explanation of the signal processing in the interferometer system. For example, as an alternative to refractive indices $n_M$ and $n_R$, other parameters which describe the refractive-index fluctuations may also be transferred from first processor unit 63 to correction unit 66.

Second Exemplary Embodiment

A second exemplary embodiment of an interferometer system is explained in the following with reference to FIGS. 3a and 3b. FIG. 3a again shows the beam path of the same; the signal processing in this variant is explained with the aid of FIG. 3b. Incidentally, the example of FIGS. 3a and 3b involves a variant which is denoted as "spectrally integrated case" in the theory section above.

The optical construction of interferometer 10 in this variant also corresponds substantially to that from the exemplary embodiment described before in FIG. 2a; therefore, a detailed description of it again is omitted.

In regard to interferometer 10 used, it should merely be mentioned as a slight difference that reference arm R is now selected to be very short, so that in particular, no detection and correction of refractive index $n_R$ in reference arm R is necessary.

A spectrometer unit 150 is again provided as a detecting device for detecting fluctuations in refractive index $n_M$ of the air in measuring arm M of interferometer 10. The spectrometer unit again includes a spectrometer light source 151 which emits bundles of rays having wavelength $\lambda_S$. The emitted bundles of rays are superimposed in measuring arm M of interferometer 10 on the measuring-arm partial bundle of rays of interferometer 10 via a beam-splitter element 153 in the form of a dichroic beam splitter. Consequently, in this example, the superimposition of the bundles of rays from spectrometer light source 151 with the measuring-arm partial bundle of rays of interferometer light source 11 first takes place downstream of first interferometer beam-splitter element 13. After the bundle of rays of spectrometer light source 151 has been reflected back via retroreflector element 16, beam-splitter element 153 splits off this bundle of rays again from the partial bundle of rays of interferometer light source 11 and guides it in the direction of a spectrometer detector element 154. Spectrometer detector element 154 in turn delivers a spectrometer signal $S_{S1}$ concerning the absorption of wavelength $\lambda_S$ in respective air component ϵ.

Therefore, in this exemplary embodiment, the beam directions of interferometer 10 and of spectrometer unit 150 extend in opposite directions relative to each other, that is, anti-collinearly. It should be indicated as an advantage of this variant that no special polarization optical components are necessary for the two wavelengths $\lambda_S$ and $\lambda_I$. Moreover, as indicated schematically in the figure, the complete optics of spectrometer unit 150 including beam-splitter element 153 may be accommodated in one separate unit. However, as a general principle, this unit should be disposed as close as possible to first interferometer beam-splitter element 13 in order to ensure a detection of refractive index $n_M$ in the most complete measuring arm M possible, and to avoid non-compensated air paths.

To increase the accuracy in detecting the refractive index, it would also be possible in principle to additionally dispose a corresponding spectrometer unit in reference arm R of interferometer 10, as well, particularly when the intention is for it to be somewhat longer.

The signal processing of the second example embodiment of the interferometer system is explained with reference to the schematic representation in FIG. 3b; components having the same functionalities as in the example of FIG. 2a are provided with identical reference numerals.

As in the first example, interferometer signals $S_{I1}$, $S_{I2}$, $S_{I3}$, $S_{I4}$ are processed by second processor unit 65, at whose output a signal OPD regarding the optical path-length difference in the interferometer is made available for further processing. Again, as in the previous example, output signals $RH_0$, $T_0$, $p_0$ of schematically indicated refractive-index determination device 64, i.e., corresponding sensors 64.1, 64.2, 64.3, are supplied to first processor unit 63, as well.

Moreover, wavelength $\lambda_S$ of spectrometer light source 151 is modulated very quickly with frequency f via first processor unit 63; in example embodiments, frequency f is approximately f=200 kHz, in general, frequency f lies in the range between 10 kHz and 10 MHz. Because of this modulation, a correspondingly rapidly modulated spectrometer signal $S_{S1}$ results. Spectrometer signal $S_{S1}$ is amplified via an amplifier element 161 and fed to two band-pass filters 167.1, 167.2. The two band-pass filters have the pass frequencies f and 2f, respectively, indicated in the figure. Downstream of band-pass filters 167.1, 167.2 is the first processor unit which, from the amplified and band-pass-filtered spectrometer signals $S_{S1}$, determines amplitudes and phase positions of these signals with the aid of a lock-in amplifier. In this context, the signal amplitude at the second harmonic 2f includes the transmission, averaged spectrally over the absorption line, in respective air component ϵ, since in each modulation period, the absorption peak is passed through twice. The difference formation of signal levels in the absorption peak and outside of the spectral line to compensate for unwanted signal influences, as explained in the first exemplary embodiment, takes place automatically here, since only the amplitudes of spectrometer signals $S_{S1}$ are detected, but not their offset. In this example embodiment, the analog averaging eliminates the need for an otherwise necessary, computing-intensive, numerical integration as is required, for example, in the first exemplary embodiment. In the second exemplary embodiment, operation of spectrometer light source 151 with a markedly higher modulation or tuning frequency f is therefore possible, which means, in particular, higher accuracy of the method may be achieved. The amplitude and phase position at fundamental wave f is supplied to an offset control for wavelength $\lambda_S$. Only if the absorption line lies centrally with respect to the wavelength modulation, is this amplitude minimal. If the offset of the wavelength modulation shifts over the absorption line, then the phase of fundamental wave f of spectrometer signal $S_{S1}$ changes by 180°, which may be utilized for the offset control. With regard to the evaluation method of this example embodiment, reference is made, for instance, to the publication "Digital phase sensitive detection for in-situ diode-laser spectroscopy under rapidly changing transmission conditions", T. Fernholz et. al., Appl. Phys. B 75, 229-236, (2002)

Third Exemplary Embodiment

Figure 4:
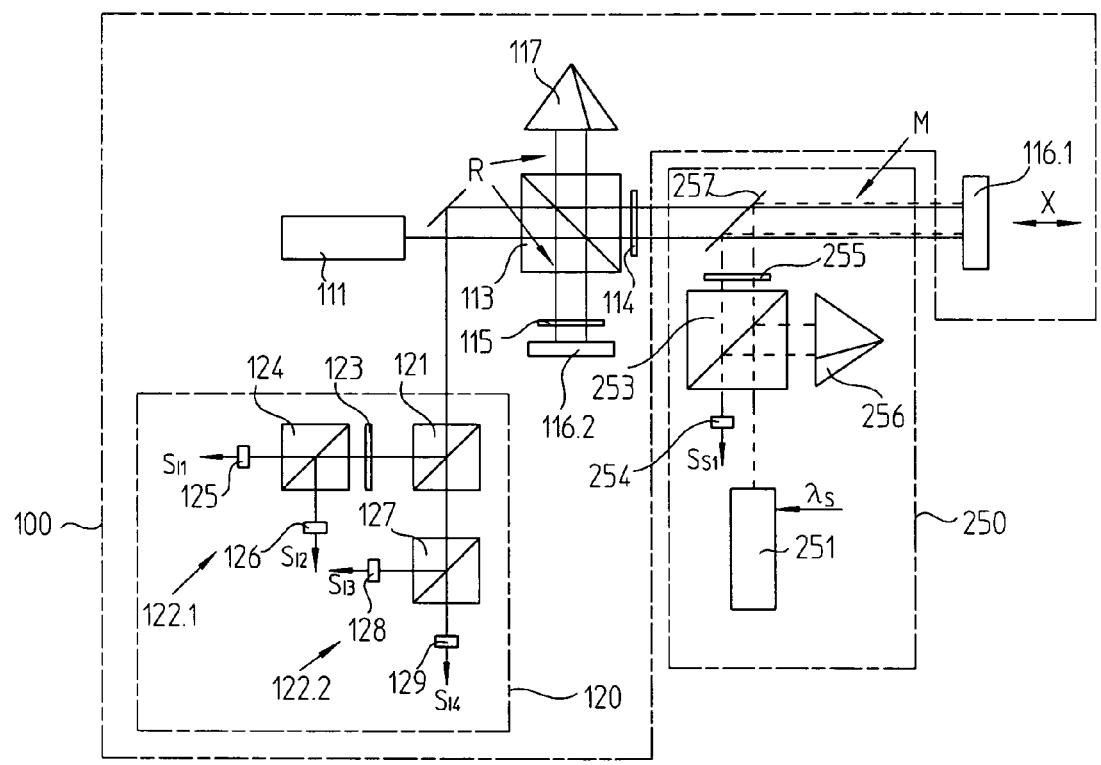
FIG. 4 shows a schematic representation of an interferometer system according to an example embodiment of the present invention.

A third exemplary embodiment of an interferometer system is explained in the following with reference to FIG. 4; since in this case, signals may in principle be processed as in the first two examples, a separate clarification of this is omitted. In contrast to the second example, the case of the third exemplary embodiment now again involves a spectrally selective variant.

As a further contrast to the two examples described previously, in this example embodiment of an interferometer system, interferometer 100 takes the form of what is referred to as a plane mirror interferometer.

In this case, a bundle of rays emitted by interferometer light source 111 is fed to a first interferometer beam-splitter element 113 in the form of a polarizing beam-splitter cube. Interferometer beam-splitter element 113 splits the incident bundle of rays into a measuring beam and a reference beam. The partial bundle of rays of the measuring beam passes through a λ/4-plate 114 in measuring arm M, is reflected at a first plane-mirror reflector element 116.1, and then passes again through λ/4-plate 114. Analogously, the partial bundle of rays of the reference beam is directed via λ/4-plate 115 to a second plane-mirror reflector element 116.2, and subsequently through λ/4-plate 115 again. Both partial bundles of rays are superimposed in interferometer beam-splitter element 113, the two partial bundles of rays being polarized orthogonally relative to each other. Both partial bundles of rays arrive at retroreflector element 117, which is in the form of a triple prism, are reflected back there and are split again because of their different polarization in interferometer beam-splitter element 113. After again passing through λ/4-plate 114, first plane-mirror reflector element 116.1 and λ/4-plate 114, or λ/4-plate 115, second plane-mirror reflector element 116.2 and λ/4-plate 115, the partial bundles of rays are finally superimposed again in interferometer beam-splitter element 113 and directed to detector unit 120 for the generation of the four phase-shifted interferometer signals $S_{I1}$, ... $S_{I4}$ in known manner. In this example, first plane-mirror reflector element 116.1 represents the measuring reflector whose position is to be measured along measuring direction x.

Spectrometer unit 250 in this example embodiment includes a spectrometer light source 251 which sends a linearly polarized bundle of rays to a spectrometer beam-splitter element 253, taking the form of a polarizing beam-splitter cube, such that this bundle of rays is transmitted exclusively. It passes through a λ/4-plate 255 and is directed via a beam-splitter element 257 in measuring arm M of interferometer 100 in collinear fashion with respect to the interferometer bundle of rays. For instance, beam-splitter element 257 is in the form of a dichroic beam splitter.

After reflection at plane-mirror reflector element 116.1 and at beam-splitter element 257, the spectrometer bundle of rays again reaches λ/4-plate 255, and is therefore reflected by spectrometer beam-splitter element 253 taking the form of a polarizing beam-splitter cube. A retroreflector element 256 reflects the spectrometer bundle of rays back in displaced fashion, so that it is reflected again at spectrometer beam-splitter element 253. It arrives again, via components 255, 257, 116.1, 257 and 255, at spectrometer beam-splitter element 253, which then transmits the spectrometer bundle of rays on the basis of the rotated polarization. It is ultimately detected by spectrometer detector element 254, which delivers a corresponding spectrometer signal $S_{S1}$. The beam displacement of retroreflector element 256 is selected such that the superimposed bundles of rays of interferometer 100 and of spectrometer unit 250 extend collinearly between plane-mirror reflector element 116.1 and beam-splitter element 257.

In this exemplary embodiment, all polarization optical components are in each case designed for only one wavelength $\lambda_I$ or $\lambda_S$, which greatly simplifies their manufacture. Spectrometer unit 250 may again be designed as a separate unit.

The signal evaluation may be performed as in the first or second example embodiment of the interferometer system. Alternatively, the wavelength of the spectrometer unit may be regulated to the absorption peak of the respective absorption line. Suitable control methods are known from the literature.

Fourth Exemplary Embodiment

A fourth exemplary embodiment of an interferometer system is explained in the following with reference to FIG. 5, which again shows a schematized representation of the different beam paths.

In principle, the fourth exemplary embodiment is based on the third exemplary embodiment of an interferometer system explained previously. Thus, in this variant, in addition to interferometer system 100 according to FIG. 4 shown in the bottom part of FIG. 5, an identical such interferometer system 100' according to the third exemplary embodiment is provided again in the upper part. Therefore, the fourth exemplary embodiment includes two interferometer systems 100, 100' according to the third exemplary embodiment.

In the same manner, in this variant, naturally two spectrometer units 250, 250' are provided which are assigned to interferometers 100, 100' and are constructed as in the previous third exemplary embodiment.

Figure 5:
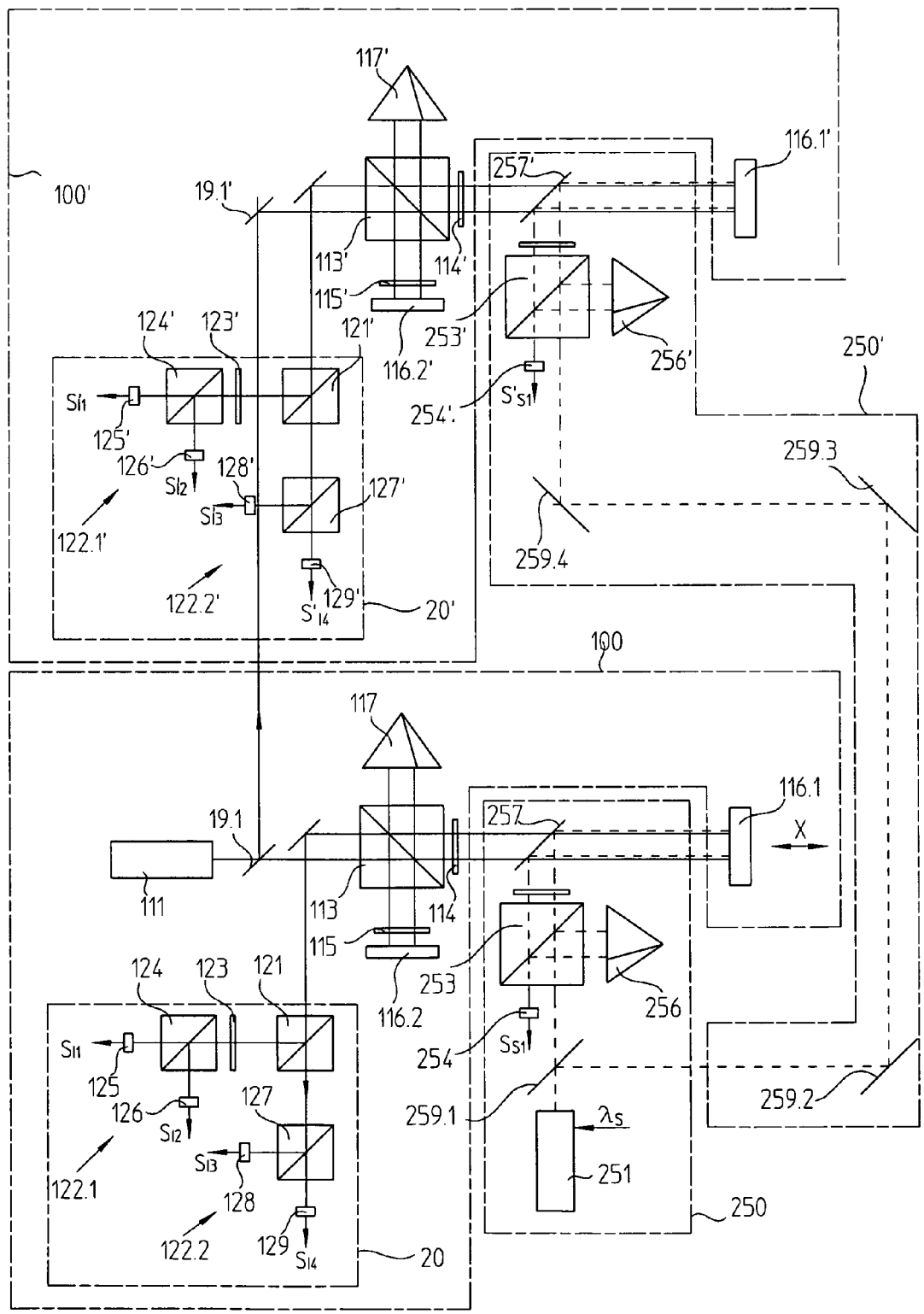
FIG. 5 shows a schematic representation of an interferometer system according to an example embodiment of the present invention.

Therefore, in the lower part of FIG. 5, the same reference numerals are used for the various components of interferometer 100 and of spectrometer unit 250 having the identical function as in the third exemplary embodiment; in the upper part, the corresponding components are provided with the mark "'".

Both interferometers 100, 100' as well as the two assigned spectrometer units 250, 250' are both fed by the same interferometer light source 111 and spectrometer light source 251, respectively. By additional beam-splitter elements 19.1, 259.1, in each case bundles of rays for the supply of additional interferometer 100' and of additional spectrometer unit 250', respectively, are split off from the bundles of rays of interferometer light source 111 and of spectrometer light source 251, respectively, and supplied via further deflecting elements 19.2 or 259.2, 259.3, 259.4 to additional units 100', 250'.

The interferometer system in the lower part of FIG. 5 having interferometer 100 and spectrometer unit 250 is used in this example as the actual measuring system; the interferometer system in the upper part of FIG. 5 having interferometer 100' and spectrometer unit 250' acts as a calibration system. Interferometer 100' of the calibration system has a fixed measuring distance known if possible, that is, plane-mirror reflector element 116.1' does not move along the measuring distance. Coefficients $\alpha_{\epsilon 0}$, $\beta_\epsilon$ and $\alpha'_{\epsilon 0}$, $\beta'_\epsilon$ from Equations 18a and 18b, respectively, may then be calibrated via the calibration system, and thus changes in the air composition may also be balanced. To that end, with the aid of Equations 2, 3 and 18a or 18b, coefficients $\alpha_{\epsilon 0}$, $\beta_\epsilon$ and $\alpha'_{\epsilon 0}$, $\beta'_\epsilon$, respectively, are determined by a linear balancing calculation such that measured geometric path-length difference GPD has the smallest root-mean-square deviation with respect to the known actual geometric path-length difference of the calibration interferometer.

Fifth Exemplary Embodiment

Figure 6:
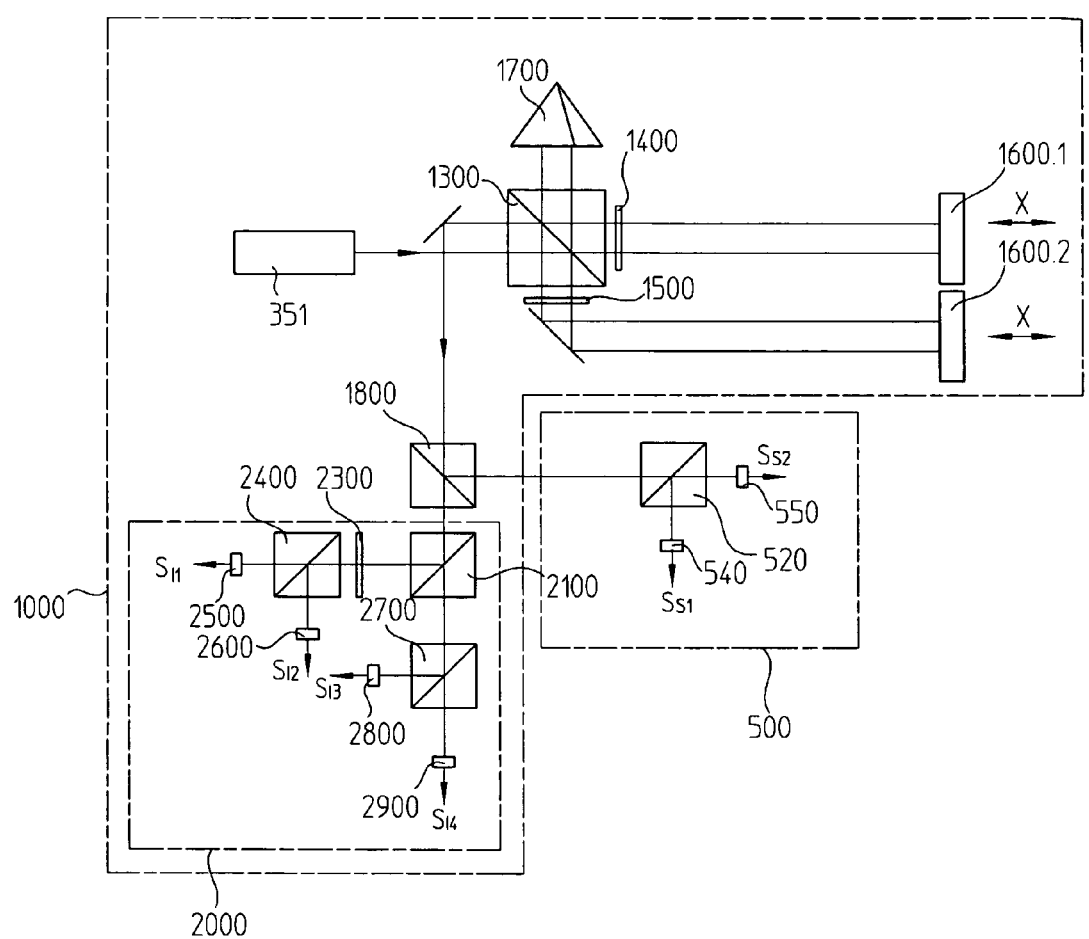
FIG. 6 shows a schematic representation of an interferometer system according to an example embodiment of the present invention.

FIG. 6 shows the schematized beam path of a fifth example embodiment of an interferometer system. Again, only the important differences with respect to the previous variants are explained in the following.

Thus, the interferometer system includes a combined interferometer/spectrometer-unit configuration which is fed from the same or a shared light source 351. That means that in this example, light source 351 acts both as the interferometer light source and as the spectrometer light source. Wavelength $\lambda_I = \lambda_S$ of light source 351 is again selected in the range of the absorption line of one air component c.

First of all, this light source 351 supplies an interferometer 1000 that takes the form of a differential plane-mirror interferometer and whose construction is similar to the interferometer in the fourth example embodiment. In contrast to that, it is merely provided that plane-mirror reference reflector 1600.2 is likewise able to be moved in measuring direction x.

The bundle of rays exiting from first interferometer beam-splitter element 1300—in the form of a polarizing beam-splitter cube—in the direction of second interferometer beam-splitter element 1800 includes the two partial bundles of rays of the measuring distance and the reference distance, having polarizations that are orthogonal relative to each other. Via second interferometer beam-splitter element 1800, formed as a non-polarizing beam splitter, a portion of this light bundle is branched off for the detection of the absorption in spectrometer detector unit 500 and is fed to a spectrometer beam-splitter element 520 in the form of a polarizing beam-splitter cube. The two partial bundles of rays are therefore directed separately to spectrometer detector elements 540, 550 and cannot interfere with each other. Thus, the absorption in measuring arm M of interferometer 1000 may be measured by spectrometer detector element 550, and the absorption in reference arm R of interferometer 1000 may be measured by spectrometer detector element 540.

As in the first example embodiment, initially a phase shift of interferometer 1000 is determined by interferometer detector elements 2500, 2600, 2800, 2900. Wavelength $\lambda_I = \lambda_S$ of light source 351 is tunable in the range of an absorption line. Preferably, the tuning is performed with a high modulation frequency f. The interferometer phase is likewise modulated by this wavelength modulation. By an averaging $<\Phi_S(\lambda_S)>$ of the interferometer phase over one modulation period or by a synchronous sampling at always the same sampling instants within the modulation period, stable phase values are obtained for the position measuring which are no longer influenced by the wavelength modulation.

By controlling the center wavelength of shared light source 351 with the aid of the absorption measurement, light-source wavelength $\lambda_I = \lambda_S$ is stabilized to the absorption line automatically. This is particularly advantageous when using a semiconductor laser as light source 351. A costly gas cell filled with rubidium, for example, as a primary standard of frequency or wavelength may be omitted here, since an air component $\epsilon$ in measuring arm and reference arm M,R, respectively, is used instead. In addition, due to the shared use of light source 351 and a large part of the interferometer components for the linear measurement and the absorption measurement, this exemplary embodiment is particularly simple, and thus inexpensive to construct.

Sixth Exemplary Embodiment

Figure 7:
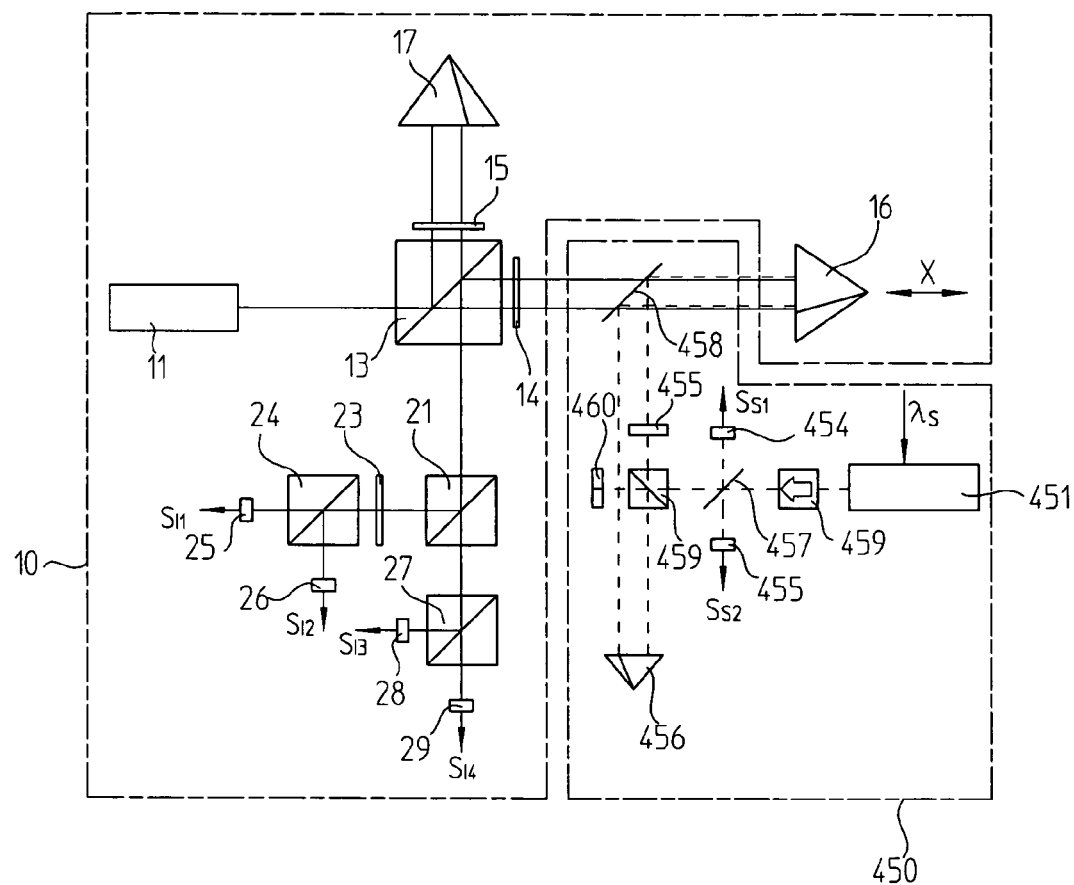
FIG. 7 shows a schematic representation of an interferometer system according to an example embodiment of the present invention.

Finally, a sixth exemplary embodiment of an interferometer system is explained with reference to the representation in FIG. 7. Again, only the important contrasts to the previous variants are discussed in the following description.

Figure 3A:
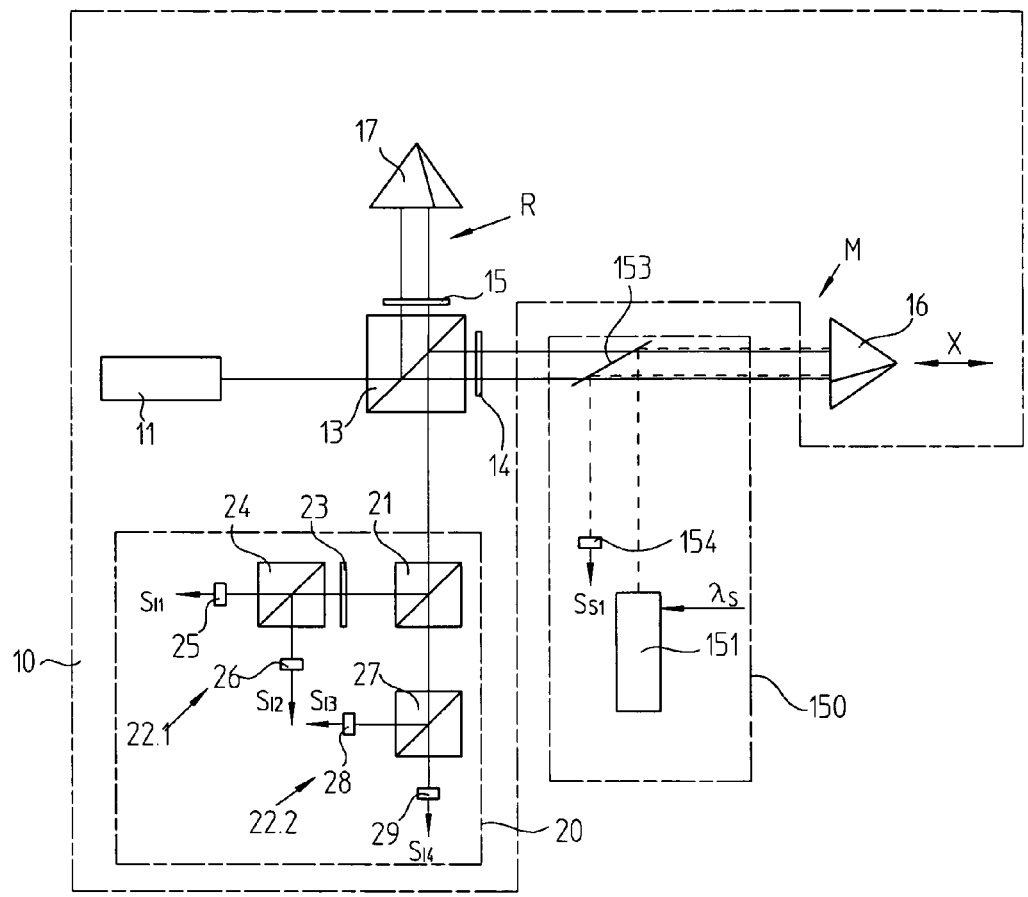
FIG. 3*a* shows a schematic representation of an interferometer system according to an example embodiment of the present invention.
Figure 3B:
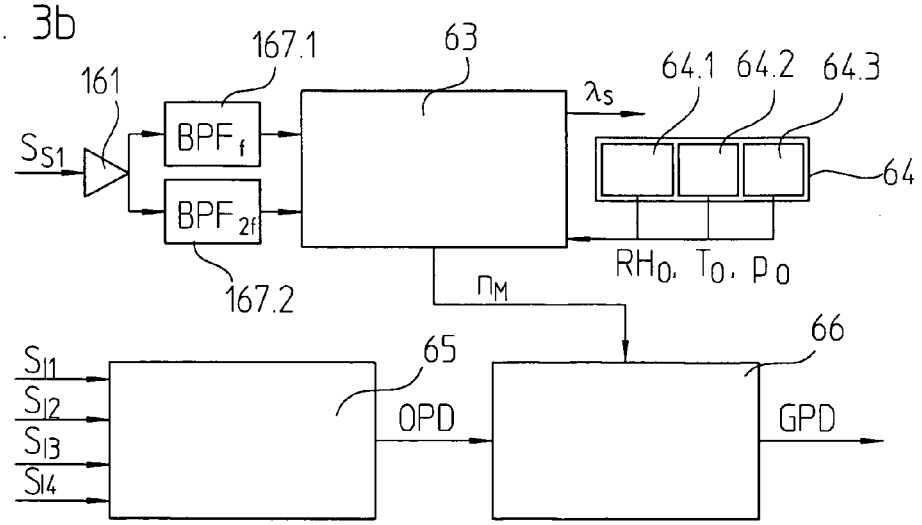
FIG. 3*b* shows a schematic representation for clarifying the signal processing of the interferometer system illustrated in FIG. 3*a*.

The set-up of interferometer 10 used in this example is identical to that from FIG. 2a or 3a, which is why a detailed description of it is omitted. Differing from the previous variants is the design of spectrometer unit 450 in this exemplary embodiment, which is explained in the following.

The bundle of rays from spectrometer light source 451 passes through an optical isolator element 459 which prevents stray light from reflecting back into the resonator of spectrometer light source 451. This permits spectrometer light source 451 to be operated in a more stable fashion. The bundle of rays from spectrometer light source 451 is subsequently split at beam-splitter element 457. A reflected partial bundle of rays is detected by a spectrometer detector element 455, and spectrometer signal $S_{S2}$ is delivered as reference signal, which represents a measure for the power of spectrometer light source 451. The transmitted partial bundle of rays from spectrometer light source 451 strikes a spectrometer beam-splitter element 453 taking the form of a polarizing beam-splitter cube. The linear polarization of the incident partial bundle of rays is selected so that the partial bundle of rays is reflected at polarizing spectrometer beam-splitter element 453. This partial bundle of rays subsequently passes through a $\lambda/2$-plate 455 which rotates the linear polarization of this partial bundle of rays by 90°, and is then reflected by beam-splitter element 458, formed as a dichroic beam splitter, and superimposed in anti-collinear fashion with the partial bundle of rays from interferometer light source 11. After retroreflection at retroreflector element 16 and reflection once more at beam-splitter element 458, the partial bundle of rays reaches retroreflector element 456 and is retroreflected there, as well. Due to the rotation of the polarization direction, the partial bundle of rays of the spectrometer passes through polarizing spectrometer beam-splitter element 453 without deflection and arrives once more, via components 455, 458, 16, 458 and 456, at polarizing spectrometer beam-splitter element 453. Due to the rotation of the polarization direction through $\lambda/2$-plate 455 again, the partial bundle of rays is reflected at spectrometer beam-splitter element 453 and reaches the mirror, i.e., retroreflector element 460, where a reflection takes place back in the direction of spectrometer beam-splitter element 453. After that, polarizing spectrometer beam-splitter element 453 reflects the partial bundle of rays again, so that the beam direction is turned around, and the partial bundle of rays passes through components 456, 458, 16, 458, 455, 453, 456, 458, 16, 458, 455. The partial bundle of rays is then reflected by polarizing spectrometer beam-splitter element 453 and arrives via beam-splitter element 457 at spectrometer detector element 454, which generates spectrometer signal $S_{S1}$.

Because of the various optical elements in the beam path of spectrometer unit 450, the measuring distance between beam-splitter element 458 and retroreflector element 16 acting as measuring reflector is traversed a total of four times back and forth in this configuration. Therefore, spectrometer signal $S_{S1}$ measures absorption effects that are four times higher than in the first exemplary embodiment, which increases the measuring accuracy considerably. In this example embodiment, spectrometer signal $S_{S1}$ is divided on the evaluation side by spectrometer signal $S_{S2}$ acting as reference signal. In this manner, compensation is made for the fluctuations in the power of spectrometer light source 451 during the modulation of spectrometer wavelength $\lambda_S$, so that resulting signal $S=S_{S1}/S_{S2}$ is determined only by the air absorption.

In addition to the exemplary embodiments specifically described, there are, of course, also alternative design possibilities within the scope hereof.

As modification of the example embodiments described above, instead of the homodyne interferometers described, it is possible in particular to employ heterodyne interferometers, as well. That is described briefly in the following on the basis of the example from FIG. 3a. In this case, interferometer light source 11 emits two collinear bundles of rays having somewhat different wavelengths, which are polarized orthogonally relative to each other. The polarization axes of interferometer light source 11 used are aligned with respect to the polarization axes of interferometer beam-splitter element 13 of the interferometer such that the one bundle of rays having the first wavelength is directed into measuring arm M, and the other into reference arm R. In this case, interferometer detection unit 20 includes only one detector having a polarizer disposed in front of it, that detects the bundle of rays fed from interferometer beam-splitter element 13. The signal delivered by the detector is modulated on the basis of the interference of the two wavelength components of interferometer light source 11. The phase of this modulation is evaluated in known manner in a suitably adapted second processor unit 65 and supplies optical path-length difference OPD. The construction of the spectrometer unit remains unaffected by this.

Furthermore, in addition to the interferometer types described, it is also possible to use other interferometer types within the interferometer system according to example embodiments of the present invention, e.g., Mach-Zehnder interferometers, grating interferometers, angular interferometers and Speckle interferometers. In particular, grating coders having a large sampling interval may also be used.

Moreover, the measures described herein, e.g., especially the provision of the spectrometer unit, may also be used in conjunction with imaging interferometers (e.g., Fizeau, Twyman-Green, . . . ) in which one or more camera sensors supply spatially-resolved length information. It is advantageous if not only the interferometer, but also the spectrometer unit is equipped with such spatially-resolving camera sensors. Thus, every pixel value of the interferometer may be corrected individually by the evaluation of associated pixel values of the spectrometer unit. The fifth example embodiment described is especially advantageous in this case, since the same light source is used for the interferometer and the spectrometer unit.

In principle, the compensation, according to example embodiments of the present invention, of fluctuations in the refractive index of air by measuring the absorption of at least one air component in the at least two beam paths of an optical system based on interference may be transferred to any such system.

In addition, it is possible to use a spectrometer light source having a spectral width which is somewhat greater than that of the absorption line used. In this case, an averaging over the spectral width takes place automatically.

Instead of the relatively costly calibration system according to the fourth example embodiment, reference measurements may also be performed by approaching reference points along the measuring distance. The reference points are indicated by signals of additional reference sensors (e.g., capacitive or optical zero-point sensors). Finally, coefficients $\alpha_{\epsilon 0}, \beta_\epsilon$ and $\alpha'_{\epsilon 0}, \beta'_\epsilon$, respectively, are in turn determined with this information.

It is further possible to provide a fiber lead for the light sources of the interferometer and/or of the spectrometer unit, in order to keep the development of heat low and to permit easy installation.

Furthermore, it may be provided, for example, to distribute the bundles of rays of the interferometer light source and/or the spectrometer light source among a plurality of interferometer axes and associated spectrometer units, respectively, in order to minimize the necessary outlay.

In addition, further modulation methods may also be employed for regulating the center wavelength, as is described, for instance, in the publication "Development of an IR tunable diode laser absorption spectrometer for trace humidity measurements at atmospheric pressure", Chr. S. Edwards et al, Appl. Optics 38, No. 21, Jul. 20, 1999.

What is claimed is:

1. An interferometer system, comprising
an interferometer including an interferometer light source, radiation emitted from the light source splittable into a measuring arm and a reference arm, an object to be measured arranged in the measuring arm, the interferometer adapted to generate interferometer signals as a function of a position of the object to be measured; and
a detection device adapted to detect fluctuations in a refractive index of air in at least one of (a) the measuring arm and (b) the reference arm;
wherein the detection device includes a spectrometer unit, the spectrometer unit including:
a spectrometer light source, bundles of rays emitted from the spectrometer light source superimposable on bundles of rays of the interferometer light source, the spectrometer light source adapted to emit radiation having a wavelength in a range of an absorption line of at least one specific air component; and
at least one spectrometer detector unit adapted to generate spectrometer signals that characterize the absorption of the air component with respect to the spectrometer light-source wavelength in at least one of (a) the measuring arm and (b) the reference arm.

2. The interferometer system according to claim 1, wherein the detection device includes a refractive-index determination device adapted to determine a nominal refractive index of the air in an area of at least one of (a) the measuring arm and (b) the reference arm.

3. The interferometer system according to claim 1, further comprising a first processor unit, an input of the first processor unit adapted to receive the spectrometer signals of the spectrometer unit, the processor unit adapted to determine the fluctuations in the refractive index of the air in at least one of (a) the measuring arm and (b) the reference arm based on the spectrometer signals and to make corresponding output signals of the first processor unit available for further processing.

4. The interferometer system according to claim 2, further comprising a first processor unit, an input of the first processor unit adapted to receive the spectrometer signals of the spectrometer unit, the processor unit adapted to determine the fluctuations in the refractive index of the air in at least one of (a) the measuring arm and (b) the reference arm based on the spectrometer signals and to make corresponding output signals of the first processor unit available for further processing, wherein the first processor unit is adapted to receive output signals of the refractive-index determination device, to determine an average refractive index in an area of at least one of (a) the measuring arm and (b) the reference arm based on the applied signals, and to make corresponding output signals of the first processor unit available for further processing.

5. The interferometer system according to claim 3, further comprising a correction unit having an input side adapted to receive the output signals of the first processor unit with respect to the refractive index in at least one of (a) the measuring arm and (b) the reference arm and output signals of a second processor unit with respect to an optical path-length difference, the second processor unit adapted to determine the optical path-length difference from applied interferometer signals, the correction unit adapted to determine from the output signals of the first processor unit with respect to the refractive index in at least one of (a) the measuring arm and (b) the reference arm, an effective refractive index and to process the effective refractive index in conjunction with the optical path-length difference, and to make corrected position signals with respect to a position of the object to be measured in the measuring arm available on an output side.

6. The interferometer system according to claim 3, wherein the first processor unit is adapted to tune a wavelength of the spectrometer light source in a range of at least one absorption line of at least one air component whose absorption characteristic is determined.

7. The interferometer system according to claim 3, wherein the first processor unit is adapted to tune a Fabry-Perot interferometer in a range of at least one absorption line of at least one air component whose absorption characteristic is determined, the Fabry-Perot interferometer arranged on a side of the spectrometer detector unit.

8. The interferometer system according to claim 6, wherein the first processor unit is adapted to control a center wavelength of the tuning range of the spectrometer light source so that a center wavelength is at a fixed distance to an absorption peak of the air component.

9. The interferometer system according to claim 7, wherein the first processor unit is adapted to tune the Fabry-Perot interferometer so that a center wavelength is at a fixed distance to an absorption peak of the air component.

10. The interferometer system according to claim 1, wherein the interferometer and the spectrometer unit have a shared light source.

11. The interferometer system according to claim 1, wherein disposed in a beam path of the spectrometer unit are optical elements adapted to guide the bundle of rays from the spectrometer light source multiple times along at least one of (a) the measuring arm and (b) the reference arm of the interferometer.

12. The interferometer system according to claim 8, wherein the first processor unit is adapted to periodically tune the wavelength of the spectrometer light source in the tuning range, the tuning period being shorter in time than a typical fluctuation of the refractive index in at least one of (a) the measuring arm and (b) the reference arm.

13. The interferometer system according to claim 1, wherein a wavelength of the spectrometer light source is in a range of at least one absorption line of at least one of the following air components: (a) $N_2$, (b) $O_2$, (c) $CO_2$, and (d) $H_2O$.

14. The interferometer system according to claim 13, wherein the wavelength of the spectrometer light source is at least in a range of an absorption line of water and one further air component.

15. The interferometer system according to claim 1, wherein the interferometer system is adapted to measure a plurality of absorption lines having sharply different temperature coefficients.

16. The interferometer system according to claim 1, wherein a spectral width of the spectrometer light source is less than or comparable to a spectral width of the absorption line.

17. The interferometer system according to claim 3, wherein the first processor unit is adapted top form, from the spectrometer signals applied on the input side, differential absorption values from an absorption in a center of the absorption line and an absorption in a periphery of the absorption line, which are usable to determine the refractive index.

18. The interferometer system according to claim 3, wherein the first processor unit is adapted to determine a spectral width of the absorption line from the spectrometer signals applied on the input side.

19. The interferometer system according to claim 1, wherein the interferometer includes an interferometer detector unit having a plurality of interferometer detector elements adapted to generate a plurality of position signals at various measuring points of the object to be measured, the spectrometer detector unit including a plurality of spectrometer detector elements adapted to detect the absorption of the air component in at least one of (a) the measuring arm and (b) the reference arm.

20. The interferometer system according to claim 19, wherein the interferometer detector elements and the spectrometer detector elements are arranged as a detector array.

21. The interferometer system according to claim 1, wherein the interferometer is arranged as at least one of (a) a Michelson interferometer, (b) a Fabry-Perot interferometer, (c) a Fizeau interferometer, (d) a Twyman-Green interferometer, and (e) a Speckle interferometer.

22. The interferometer system according to claim 1, wherein the spectrometer detector unit includes a tunable Fabry-Perot interferometer.

23. The interferometer system according to claim 1, wherein the spectrometer light source includes at least one of (a) a DFB laser and (b) an external cavity laser.

24. The interferometer system according to claim 2, wherein the refractive-index determination device includes at least one of (a) at least one sensor adapted to determine air parameters and (b) a reference interferometer having a known measuring distance adapted to determine an average refractive index of the air in at least one of (a) the measuring arm and (b) the reference arm.

25. A method for operating an interferometer system, comprising:
  splitting emitted radiation from an interferometer light source of an interferometer into a measuring arm and a reference arm;
  arranging an object to be measured in the measuring arm;
  generating interferometer signals by the interferometer as a function of a position of the object;
  detecting, by a detection device, fluctuations in a refractive index of air in at least one of (a) the measuring arm and (b) the reference arm, the detection device including a spectrometer unit;
  emitting radiation from a spectrometer light source of the spectrometer having a wavelength in a range of an absorption line of at least one air component;
  superimposing bundles of rays emitted by the spectrometer light source on bundles of rays of the interferometer light source; and generating, by at least one spectrometer detector unit, spectrometer signals that characterize the absorption of the air component in terms of the spectrometer light-source wavelength in at least one of (a) the measuring arm and (b) the reference arm (M, R).

26. The method according to claim 25, further comprising determining, by a refractive-index determination device of the detection device, a nominal refractive index of the air in an area of at least one of (a) the measuring arm and (b) the reference arm.

27. The method according to claim 25, further comprising:
determining fluctuations in the refractive index of the air in at least one of (a) the measuring arm and (b) the reference arm from the spectrometer signals; and
making corresponding signals available for further processing.

28. The method according to claim 26, further comprising:
determining fluctuations in the refractive index of the air in at least one of (a) the measuring arm and (b) the reference arm from the spectrometer signals;
making signals corresponding to the determined fluctuations available for further processing;
determining an average refractive index in an area of at least one of (a) the measuring arm and (b) the reference arm; and
making signals corresponding to the determined average refractive index available for further processing.

29. The method according to claim 27, further comprising:
determining, based on signals with respect to the refractive index in at least one of (a) the measuring arm and (b) the reference arm, an effective refractive index is determined;
processing the determined effective refractive index in conjunction with an optical path-length difference determined from the interferometer signals; and
making available for further processing corrected position signals with respect to the position of the object to be measured in the measuring arm.

30. The method according to claim 25, further comprising tuning a wavelength of the spectrometer light source in a range of at least one absorption line of at least one air component having at least one of (a) an absorption characteristic and (b) a dispersion characteristic that is determined.

31. The method according to claim 25, further comprising tuning a Fabry-Perot interferometer in a range of at least one absorption line of at least one air component having at least one of (a) an absorption characteristic and (b) a dispersion characteristic that is determined, the Fabry-Perot interferometer being arranged on a side of the spectrometer detector unit.

32. The method according to claim 30, further comprising controlling a center wavelength of a tuning range of the spectrometer light source so that the center wavelength is at a fixed distance to an absorption peak of the air component.

33. The method according to claim 32, further comprising tuning the wavelength of the spectrometer light source periodically in the tuning range, the tuning period being shorter in time than a typical fluctuation of the refractive index in at least one of (a) the measuring arm and (b) the reference arm.

34. The method according to claim 27, further comprising:
forming, based on the spectrometer signals, differential absorption values from an absorption in a center of the absorption line and an absorption in a periphery of the absorption line; and
determining the refractive index in accordance with the differential absorption values.

35. The method according to claim 27, further comprising determining a spectral width of the absorption line from the spectrometer signals.

* * * * *